US 007157570B2

(12) United States Patent
Yen

(10) Patent No.: US 7,157,570 B2
(45) Date of Patent: Jan. 2, 2007

(54) HUMAN RIBONUCLEOTIDE REDUCTASE M2 SUBUNIT

(76) Inventor: Yun Yen, 1301 Oaklawn Rd., Arcadia, CA (US) 91006

( * ) Notice: Subject to any disclaimer, the term of this patent is extended or adjusted under 35 U.S.C. 154(b) by 476 days.

(21) Appl. No.: 10/396,678

(22) Filed: Mar. 25, 2003

(65) Prior Publication Data

US 2003/0224414 A1 Dec. 4, 2003

Related U.S. Application Data

(60) Provisional application No. 60/368,685, filed on Mar. 29, 2002.

(51) Int. Cl.
*C07H 21/02* (2006.01)
*C07H 21/04* (2006.01)
(52) U.S. Cl. .................. 536/24.1; 536/23.1; 536/24.3; 536/24.31; 435/320.1; 435/252.3
(58) Field of Classification Search .................. None
See application file for complete search history.

(56) References Cited

U.S. PATENT DOCUMENTS 6,812,339 B1 * 11/2004 Venter et al. ............ 536/24.31

OTHER PUBLICATIONS

Zhou et al. NCBI Database, National Center for Biotechnology Information, NIH (Bethesda, MD, USA) GenBank Accessioon No. AY032750, May 12, 2001.*
Park et al. NCBI Database, National Center for Biotechnology Information, NIH (Bethesda, MD, USA) GenBank Accession No. AF149206, Feb. 18, 2000.*
Osoegawa et al. Genomics 1998. 52: 1-8.*
GenBank Accession No. AC104794. NCBI Database, National Center for Biotechnology Information, NIH (Bethesda, MD, USA) Dec. 21, 2001.*
Pieter de Jong email (Jun. 12, 2002).*
Maria Pellegrini et al. "Structure-Based Optimization of Peptide Inhibitors of Mammalian Ribonucleotide Reductase". Biochemistry, 39:12210-12215, 2000.
Jae B. Park et al. "Characterization of the Promoter of the Human Ribonucleotide Reductase R2 Gene". Biochemical and Biophysical Research Communications 264:651-657, 2000.
B. Zhou et al. "Characterization of the human ribonucleotide reductase M2 subunit gene; genomic structure and promoter analyses". Cytogenet. Cell. Genet. 95:52-59, 2001.
B. Zhou et al. "Human ribonucleotide reducatase M2 subunit gene amplification and transcriptional regulation in a homogeneous staining chromosome region responsible for the mechanism of drug resistance". Cytogenet. Cell. Genet. 95:34-42, 2001.

* cited by examiner

*Primary Examiner*—Carla J. Myers
(74) *Attorney, Agent, or Firm*—Fish & Richardson P.C.

(57) ABSTRACT

An isolated nucleic acid containing a human ribonucleotide reductase M2 subunit promoter sequence or genomic sequence. Also disclosed are methods of determining whether a subject is suffering from or at risk for developing a cell proliferation-associated disorder, identifying a compound for treating a cell proliferation-associated disorder, treating a cell proliferation-associated disorder, and developing a procedure for treating a cell proliferation-associated disorder.

12 Claims, No Drawings

SEQUENCE LISTING

<160> NUMBER OF SEQ ID NOS: 59

<210> SEQ ID NO 1
<211> LENGTH: 10304
<212> TYPE: DNA
<213> ORGANISM: Homo sapiens

<400> SEQUENCE: 1

```
ccccgagccg cggtttctcc accctaatgg tgaacagcct tttggaagtc gcgctaacct      60
tggcctgaga cctgcaaact tgcccaggct ggggcgtgtg aaccggcgag cgcgcagcgg     120
aaacggggcg gggcacctga ggctgggaat gcagaggagc cttccggggg gcggggcggg     180
gcctcccgtg cataccaatg gtggggtaga ttcaaatgtc aattcgcgcg ctcaagtggc     240
ttccgccagg aatcccgacc cttatggaag cggaaggaag atcgcttgat accaacctgg     300
gctagctagc gagacctcgt ctgtttactt aaataaaacc aaaaaaacga gcaccgaggg     360
aaaaaggagt gaatcccggg gctagcagca gcctgcggcg ggcgctctcc cgggagtggc     420
tgcaccgccc gacctccccg gaggcggaac cgcccgcatt gccgcgtggc cctgggcgcc     480
gccacctcct ccgcagcggg gcaaagttgc cggacctggg ggcaggaggg ccacgccgag     540
atgactcagg tttagcgcgg gaggggagga tggcgacttc acccggcctt taacaacacg     600
tacgcatctt tcggcgtctt ctacaatggc tatgttaatt acgtggccag gaactaaact     660
atcaatgaag ccacctctga ctacttcagt tacagtgagt ttaacaggag caaaaaagca     720
cgtggcgccc tagggcaacc gaaacgaggg ttttagacgc tgattatggg aaattgaaat     780
ctgagttgag tatgagatga caccaataaa ttataatttt gttagataat agctttatca     840
gccataaagt aatcaataaa aataccagtt tcctggagat ggatgcttta gtgtgtttgg     900
ggtgaaaatg gcgatgaatg gcgagttgct ttaaacaaat catggtacac caaagttta      960 gttgtggctt tgtgtaagga atgtgatggg cacttattcc tgcaacacga gaatactatg    1020
atttacaagt ccgtagtact tttaagaaat gagagaaaca gacctaggtg gggagggtac    1080
ctgtcccacc ccaccctctt taaagtatct tatctagaaa aggctttgtg aaaaaaaaag    1140
tcccgggtct ctctcaataa cagccctgag cgcagctgtt gaagctttct caggttaatg    1200
atttctttct tggatcttaa agtttctttc tcttcctta tttttggcat tttgcccgtt    1260
```

-continued

| | |
|---|---|
| gcagggcctg gcaaatcaga aagccacata gaaaattaaa tgaaagctat tgctaagttc | 1320 |
| cagtctctac accagtggag ttttcaaact cctcttcagc atatttgacg cccaatgagt | 1380 |
| agtacattaa ttcctagtcc taaaatcatt ctgtgaactt tctcccagga atttttgctc | 1440 |
| agtttgcaat taaaacaact ttttttcttc tcttttttaat ggcagaggcg gggtctcact | 1500 |
| atgttgccca ggatggtctc cagctcctgg cctcaaacaa tcctcctgcc ttggcctccc | 1560 |
| aaagtgctgg gattacaggc gtgagccacc gcgcccagcc acagtttgca attcttaagg | 1620 |
| caagggtgac aatagggtc aggggtctga caggagacag gatttctgtg gaaaactgca | 1680 |
| ccaagggcct tctcgccatg tcccgtagtt tgaaggttta caaggactg cacattttac | 1740 |
| atgagtcatc tcaacgaacg ctctcctcac cgcattaaca gtccacgcgg ttacgagtcc | 1800 |
| cattttactc acgggacac cgaatctgta agaagcctgg tcgcttgtcc cagcaaaacg | 1860 |
| agccacgggg ctcagcggcc ctaacttta ggctgtaggg tcctcgccga ccaccccgcc | 1920 |
| aaaatgtcag gcctcgggc ccttgcaccc caccgcagg acacggatc gaaagggtcg | 1980 |
| cagcaacgcc tcccccgcac ccaggagcgt tttccaggcc tttgcaccaa cctcgttggc | 2040 |
| taagccccct gccggcggc ggcccggctg ggaggaggtg ctttcgggag gcggggccgc | 2100 |
| ggcccgggga tcctctcgcg cccgcgggct ccaatcgctg ctcctcacgc aatcctaaac | 2160 |
| ggttcccggg cgaaccgggg cccgcgcgcg ccaaggccgc cgagaccctc agggggctgcg | 2220 |
| gccctggtcc cgcgggacct gtgggggcct gggcggcggc gccccgacc cagccagcgg | 2280 |
| acgggccggg gggggaaccg ggaggtcccg ggggcgtcc acggggtgt ccccgggggt | 2340 |
| ctccggaagg cgccggcgga ggctcccgcg ctgcgcttga aaatcgcgcg cggccccgcg | 2400 |
| gccagcctgg gtaggggcaa ggcgcagcca atgggaaggg tcggaggcat ggcacagcca | 2460 |
| atgggaaggg ccggggcacc aaagccaatg ggaagggccg ggagcgcgcg gcgcgggaga | 2520 |
| tttaaaggct gctggagtga ggggtcgccc gtgcaccctg tcccagccgt cctgtcctgg | 2580 |
| ctgctcgctc tgcttcgctg cgccgccact atgctctccc tccgtgtccc gctcgcgccc | 2640 |
| atcacggacc cgcagcagct gcagctctcg ccgctgaagg ggctcagctt ggtcgacaag | 2700 |
| gagaacacgg tgagcccgcg gggagggcgc tgcgggcagg ggagggaggc agggaaagcg | 2760 |
| aagccgctcc tcactcacac gcgtctcccc gcagccgccg gccctgagcg ggacccgcgt | 2820 |
| cctggccagc aagaccgcga ggaggatctt ccaggagccc acggagccgg tgagtggcgg | 2880 |
| gcgtggggca gaggggccag ggacggcctt gggcgtcttg gcgccaaagc cgcattgttt | 2940 |
| cctcagctgt tcacactccc gccccggctc ctttcccgcc taggcggccc ctccccaggg | 3000 |
| ctgcctcccg cgcccctcgg cccatttccc ggttcgggcg tgcgctcctc tgctgcgacc | 3060 |
| cacggagtgc gacgggacag ccacgttttc acatcgggcc ccgtgaaatt gccgccaatg | 3120 |
| gaaaggactt ggtccagaaa aacgttagtt tcatatggtt cgcccggtac ttaaatgttt | 3180 |
| tattttctcc cccaacagaa aactaaagca gctgccccg gcgtggagga tgagccgctg | 3240 |
| ctgagagaaa accccgccg ctttgtcatc ttccccatcg agtaccatga tatctggcag | 3300 |
| atgtataaga aggcagaggc ttccttttgg accgccgagg aggtaatcgg aggacccag | 3360 |
| aagacccctg caggggtgac cgtcacgcct cagacataaa tgcacttgga ggttcccgtt | 3420 |
| ggcaaggggg gctaactgtg gggcatagta agtggtgcca gcatacttaa agtttgagtg | 3480 |
| ctcagtgtga gtcctgtagg ctttactctc ttcctttttat gctaaaattg tgacttccga | 3540 |
| acctcaggtg acctctccaa ggacattcag cactgggaat ccctgaaacc cgaggagaga | 3600 |
| tattttatat cccatgttct ggctttcttt gcagcaagcg atggcatagt aaatgaaaac | 3660 |

-continued

```
ttggtgagtt tccaaaacat ctttcattca tttgacgttg acgatctgag gtcgaactag    3720
ttcgctttcc tcgtcttgta cgttttccca tgctgagtgc atctgtgtgt gtaagctggg    3780
tttttatatta catggcattt cctgttttgt aacactttgc agttcttct tatggtattt    3840
tcccgactct agagaagctg agacaatatt aagtggtagc aatgtgatga ctctttgtgg    3900
ccaccacatc tgcccctct ttttttttt ttttttgagac agagtctcac tctgcccag     3960
gctggagtgc agtggcgtga tcttggctca ctgcaacctc cgcctcctgg gttcaagcga    4020
tccccaacc tcagcctcat gagtacctgg gattacagac gtgcgccacc atgcctagct    4080
aatatctgta ttttagtag agacagggtt ttaccatgtt ggccaggctg gtctcgaact    4140
gctgacctca ggtgatccac ccaccttggc ctcccaaagt gttgggatta caggcgtgag    4200
ccaccacgcc cggctctgct ccctcctttt tgtggctttg ctgttttaat aataatttgg    4260
ttgtatctct tattgcgaat ggatctttct tgacataaat taattaggaa atcgagcgct    4320
cacaaatcct attttatatg tatctatttc ctgatatgta agttgagcat atgacataaa    4380
atatcaaaga actgtgacaa attggatgaa atatatatag aaataaacct tataatggta    4440
caaagagtgc gatgctgcca gtatccgttg acagttgctg ctgttggttt tttctcaagc    4500
ttaactttga tgtgttttgc cactaggtgg agcgatttag ccaagaagtt cagattacag    4560
aagcccgctg tttctatggc ttccaaattg ccatggaaaa catacattct gaaatgtata    4620
gtcttcttat tgacacttac ataaaagatc ccaaagaaag gtgagtattc aagtggtatg    4680
ccaagatttt taggactcac taattgttga tttattacac attttagtt cacctaggga    4740
taaaaatgac tccagaatga ctaagacagt cataggcatt cccagcaccc gtggtcatgt    4800
ctgctcttag caaggggcct aaatgcactt tattattcac ttagagttgt gaaggtactc    4860
cttttaaagt tggatgtcta ccaatgtaaa accttcttt gaaaaaattc ctagatgttg     4920
ggtaagacaa actaaaacct atgtctgacc atctttgctc atttggtaaa gttgttgaga    4980
agctagaatg tggggctgca gtgggatgga cggggaagga cttgcctcct aagaagcctg    5040
cagtatagta taggcaaata agacttagta ggagttacat aaggcagagg cagcagtgaa    5100
ccctgagact gatttaggca tgcaggagtt tggctgaata aaggtagctt aaggtctgtt    5160
ttgttttgga gattggaggt gggggatta gaaatgggct gctggagtag tctagataca    5220
aaggtcagct ttagggtggc gcgcggtggt tctcgcctgt aatcccagca ctttgggagg    5280
ctgaagcggg cggacaatga ggtcaggaga tcgagaccat cctggctaac acggtgaaac    5340
cccgtctcta ctaaaaataa aaaaagtggt ggcgggcgcc tgtagtccca gctgcttggg    5400
aggctgagac aggagaatgg cgtgaacccg ggaggcggag cttgcgctcc agcctgggtg    5460
acagagcaag actccgtctc aaaaagcaaa acaaacaaa aaaacaaag gtcagctttg    5520
gggaccagaa ccttgtatgg agtggaagtg gtgaagctgc aacctaaagt agccgttgta    5580
gactttgaag tacatgaaga ggaaaagtgg taacttgaaa ggactgagga acattggga    5640
gtaaagagat ttgaacatgt ttataggtgg aaattgagaa aagaaggcaa agattagggg    5700
tacgatcggg ggcaaatgcc cagaagggga acaggaaggt ctgctgggga agcctcaaaa    5760
acaaggagga ggcagaccca ggtctcagag agagggacag tgagatggaa agaatgaacg    5820
acagctgggc atggtagtct gagctagtag tcccagctac ttgcaggct gaggcagaag     5880
gatggcttga gccctggagt ttggttttac cgtgagctgt gatcatctcg ctgcactcta    5940
gcctgggcaa cagagtgaga ccctcatctc tttaaaaaaa aaaaaaaaaa aaaaaaaaa    6000
```

-continued

```
gggtctggtg cccttggctt cagaacacaa agtcatctgg gtaggaacag tctgggaaat    6060
gagtagcctc tcaaggtggg caccagaata aagggaggca gaggagggtg gtaagggaga    6120
tccagttaac tgtagtaccc atggatttgc tttcctgacc tgggatcgac agtgtagcac    6180
agagtcacta gtaggaagca atcttagttt attggtttaa ttattttatg atatagatgt    6240
ggcaactgag gccaaataat gcacctaatc atagtctgat aatagcacag cagttaggat    6300
tttatggttc ttcaaattta aattctatga ttcttcaaat tgaacaatga tctggacttg    6360
aaataatttt aaaggcaaca aatgtccctg ctgtactgga ctatgtttta ctgtctgtag    6420
accctgaagc tcaatatgaa ctacagaata cccaaacttg tattaatgta aatcaagtgt    6480
tgaggttttt aaaagaacac tggagggaaa aactgaccag taaaaataaa acatttcggt    6540
gtgagttctt cctttaggaa gaggattggc aaatacttga atttggcctt tgtcccactt    6600
atctagcagt tggtaatcgg aggtctttta ctgtaatgct tcaattgctg ataccgtatg    6660
tgcctactag ggaatttctc ttcaatgcca ttgaaacgat gccttgtgtc aagaagaagg    6720
cagactgggc cttgcgctgg attggggaca agaggctac ctatggtaag gagacccttg    6780
cccctactta aacctgagct tcattttcca gtaatgtta ctggattttt ggcccttgaa    6840
taccaactca ctagaatcat gttggtgttt aactcctaaa taggtgaacg tgttgtagcc    6900
tttgctgcag tggaaggcat tttcttttcc ggttcttttg cgtcgatatt ctggctcaag    6960
aaacgaggac tgatgcctgg cctcacattt tctaatgaac ttattagcag agatgaggtg    7020
agtctaagtc aaataatagg gtgacctaaa ccccaaacac aactcgggca tgctcttgtg    7080
ttcactgacg gggacctgag atgctagatg gcatatatcc acatttaatg tgtgagttca    7140
accatacaca tacttgacaa aagaaggaaa tactttcatt tactgaaact gttttacttg    7200
cattctcaat atattgtaat acatttgtac atatgtattc ccctataggc tttgaatgca    7260
taaaactaca agttctttgt tttttgaggt gacggaatct tgctctgtcg ttccaggctg    7320
gagtgcaatg gcgtgatctt ggctcactgc aacctctgcc tcctaggttc aagtgattct    7380
cccgcctcag cctcccaagt agctgggatt gtaggtgcct gccaccatgc ccagctaatt    7440
ttcgtctttt tatacagacg gggtttcacc atgtttgcca gactggggtt gaactcctga    7500
cctcaggtga tcaggtgatc cacccgcctc ggcctcccag agtgctggga ttataggcat    7560
gagccaccat gcccagccaa aactacaagt tattgatggg attgggattt taagggatgt    7620
tttattattt ttgcctggta ttaatatgtt atccctttt ccgtaaaaat gttcatagta    7680
gagccaggag cggtggctca tgcctgtaat cccagcactt tggtaggccg aggcgggtgg    7740
atcatgaggt caggagattg agaccatcct ggctaacacg gtgaaacccc atctctacta    7800
aaattacaac aaaattagcc gggtatggtg gacgtgccta ttgtcccagc tacttgagag    7860
gctgacgtag gagaatcgcc tgaaacctgg aaagtggaag gtttgcagtg gagtccgaga    7920
tcacaacaca ctgcactcca gcctgggtga cagtcccccc gaaaagaat gttcatagta    7980 gccattatgt ttctcctgtt tgatctagaa attgcccctc tacttcaata ttaataagca    8040
tttcaatgaa atgagtatac attttggtct agtgtatgtc tttgattaag tcacatttga    8100
aaagccagga gcatgaactc catcttactt ggagcccagt gggcaaatca aatatggtta    8160
ccttgtagga gggcttcctt actggattgg gagataagct gtgaagcttg atgtttaatg    8220
cagtaacttg caaacttgat ttacttgaaa ttgcatacaa tttcctgagc atctaaaaac    8280
tagcttatta ctgagctttg ccttttcctg ctgggagtag tggcaaaatt agcactcatg    8340
gctgtagaaa gatcactgag tgaagctctg actcctcctt tgccaaacac acagcagagc    8400
```

```
aagaaataca ccttgcctgt cttcatctag gtggcaactt tgagggtctt gaatgggact    8460
gagcttgcct tggtggtgac atcagcagag aagtcagtag ttgaagtcat cttcccttg     8520 agagttcaag tgctctcagt atggctgagc atgttggata aggagaatgc agaaaaggac    8580
aaagtaattt catattacca tgttaatgac agaagtcttc tggctttagt gatcttgaac    8640 tttttttct agggtttaca ctgtgatttt gcttgcctga tgttcaaaca cctggtacac     8700
aaaccatcgg aggagagagt aagagaaata attatcaatg ctgttcggat agaacaggta    8760
aagtgggtga tgaaatgggt cactcaagct tgctagaaaa tgcctgtgct ttagttgtat    8820
tcagaagctg tattttggtt cctaggagtt cctcactgag gccttgcctg tgaagctcat    8880
tgggatgaat tgcactctaa tgaagcaata cattgagttt gtggcagaca gacttatgct    8940
ggaactgggt tttagcaagg taaagtattg tttacatagc cttttgcttg ttttgaagct    9000
ggtgctctgt atttatatct tgatgtgaac ccttttcagg ttttcagagt agagaaccca    9060
tttgacttta tggagaatat ttcactggaa ggaaagacta acttctttga aagagagta     9120 ggcgagtatc agaggatggg agtgatgtca agtccaacag agaattcttt taccttggat    9180
gctgacttct aaatgaactg aagatgtgcc cttacttggc tgattttttt tttccatctc    9240
ataagaaaaa tcagctgaag tgttaccaac tagccacacc atgaattgtc cgtaatgttc    9300
attaacagca tctttaaaac tgtgtagcta cctcacaacc agtcctgtct gtttatagtg    9360
ctggtagtat cacctttgc cagaaggcct ggctggctgt gacttaccat agcagtgaca     9420
atggcagtct tggctttaaa gtgaggggtg accctttagt gagcttagca cagcgggatt    9480
aaacagtcct ttaaccagca cagccagtta aaagatgcag cctcactgct tcaacgcaga    9540
ttttaatgtt tacttaaata taaacctggc acttacaaa caaataaaca ttgttttgta     9600
ctcacggcgg cgataatagc ttgatttatt tggtttctac accaaataca ttctcctgac    9660
cactaatggg agccaattca caattcacta agtgactaaa gtaagttaaa cttgtgtaga    9720
ctaagcatgt aatttttaag ttttatttta atgaattaaa atatttgtta accaacttta    9780
aagtcagtcc tgtgtatacc tagatattag tcagttggtg ccagatagaa gacaggttgt    9840
gtttttatcc tgtggcttgt gtagtgtcct gggattctct gcccctctg agtagagtgt     9900 tgtgggataa aggaatctct cagggcaagg agcttcttaa gttaaatcac tagaaattta    9960
ggggtgatct gggccttcat atgtgtgaga agccgtttca ttttatttct cactgtattt    10020
tcctcaacgt ctggttgatg agaaaaaatt cttgaagagt tttcatatgt gggagctaag   10080
gtagtattgt aaaatttcaa gtcatcctta acaaaatga tccacctaag atcttgcccc    10140
tgttaagtgg tgaaatcaac tagaggtggt tcctacaagt tgttcattct agttttgttt    10200
ggtgtaagta ggttgtgtga gttaattcat ttatatttac tatgtctgtt aaatcagaaa    10260
ttttttatta tctatgttct tctagatttt acctgtagtt catt                    10304
```

<210> SEQ ID NO 2
<211> LENGTH: 403
<212> TYPE: DNA
<213> ORGANISM: Homo sapiens

<400> SEQUENCE: 2

```
cgaccacccc gccaaaatgt caggcctcgg ggcccttgca cccccaccgc agggacacgg      60
atcgaaaggg tcgcagcaac gcctcccccg cacccaggag cgttttccag gcctttgcac    120
caacctcgtt ggctaagccc cctgcccggc ggcggcccgg ctgggaggag gtgctttcgg    180
```

-continued

```
gaggcggggc cgcggcccgg ggatcctctc gcgcccgcgg gctccaatcg ctgctcctca      240
cgcaatccta aacggttccc gggcgaaccg gggcccgcgc gcgccaaggc cgccgagacc      300
ctcaggggct gcggccctgg tcccgcggga cctgtggggg cctgggcggc ggcgcccccg      360
acccagccag cggacgggcc ggggggggaa ccgggaggtc ccg                        403
```

<210> SEQ ID NO 3
<211> LENGTH: 202
<212> TYPE: DNA
<213> ORGANISM: Homo sapiens

<400> SEQUENCE: 3

```
ccgcgctgcg cttgaaaatc gcgcgcggcc ccgcggccag cctgggtagg ggcaaggcgc      60
agccaatggg aagggtcgga ggcatggcac agccaatggg aagggccggg gcaccaaagc     120
caatgggaag ggccgggagc gcgcggcgcg ggagatttaa aggctgctgg agtgaggggt     180
cgcccgtgca ccctgtccca gc                                              202
```

<210> SEQ ID NO 4
<211> LENGTH: 660
<212> TYPE: DNA
<213> ORGANISM: Homo sapiens

<400> SEQUENCE: 4

```
cgaccacccc gccaaaatgt caggcctcgg ggcccttgca ccccaccgc agggacacgg       60 atcgaaaggg tcgcagcaac gcctccccg cacccaggag cgttttccag gcctttgcac      120
caacctcgtt ggctaagccc cctgcccggc ggcggcccgg ctgggaggag gtgctttcgg     180
gaggcggggc cgcggcccgg ggatcctctc gcgcccgcgg gctccaatcg ctgctcctca     240
cgcaatccta aacggttccc gggcgaaccg gggcccgcgc gcgccaaggc cgccgagacc     300
ctcaggggct gcggccctgg tcccgcggga cctgtggggg cctgggcggc ggcgcccccg     360
acccagccag cggacgggcc ggggggggaa ccgggaggtc ccggggggcg tccacggggg     420
tgtccccggg ggtctccgga aggcgccggc ggaggctccc gcgctgcgct tgaaaatcgc     480
gcgcggcccc gcggccagcc tgggtagggg caaggcgcag ccaatgggaa gggtcggagg     540
catggcacag ccaatgggaa gggcggggc accaaagcca atgggaaggg ccgggagcgc     600
gcggcgcggg agatttaaag gctgctggag tgaggggtcg cccgtgcacc ctgtcccagc     660
```

<210> SEQ ID NO 5
<211> LENGTH: 7
<212> TYPE: PRT
<213> ORGANISM: Artificial Sequence
<220> FEATURE:
<223> OTHER INFORMATION: synthetically generated peptide

<400> SEQUENCE: 5

Phe Thr Leu Asp Ala Asp Phe
 1               5

<210> SEQ ID NO 6
<211> LENGTH: 21
<212> TYPE: DNA
<213> ORGANISM: Homo sapiens

<400> SEQUENCE: 6

```
atttagaagt cagcatccaa g                                                21
```

<210> SEQ ID NO 7

```
<211> LENGTH: 24
<212> TYPE: DNA
<213> ORGANISM: Homo sapiens

<400> SEQUENCE: 7
tacacaaacc atcggaggag agag                                              24

<210> SEQ ID NO 8
<211> LENGTH: 20
<212> TYPE: DNA
<213> ORGANISM: Homo sapiens

<400> SEQUENCE: 8
ggctcctgga agatcctcct                                                   20

<210> SEQ ID NO 9
<211> LENGTH: 18
<212> TYPE: DNA
<213> ORGANISM: Homo sapiens

<400> SEQUENCE: 9
ctgctgcggg tccgtgat                                                     18

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
gatcgcttga taccaacctg gg                                                22

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
ggccacgccg acatgactca                                                   20

<210> SEQ ID NO 12
<211> LENGTH: 18
<212> TYPE: DNA
<213> ORGANISM: Artificial Sequence
<220> FEATURE:
<223> OTHER INFORMATION: primer

<400> SEQUENCE: 12
tccctgggag atggatgc                                                     18

<210> SEQ ID NO 13
<211> LENGTH: 18
<212> TYPE: DNA
<213> ORGANISM: Artificial Sequence
<220> FEATURE:
<223> OTHER INFORMATION: primer

<400> SEQUENCE: 13
aagcctggaa aacgctcc                                                     18

<210> SEQ ID NO 14
<211> LENGTH: 23
```

```
<212> TYPE: DNA
<213> ORGANISM: Artificial Sequence
<220> FEATURE:
<223> OTHER INFORMATION: primer

<400> SEQUENCE: 14
tcccgtagtt tgaaggttta caa                                           23

<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15
actccagcag cctttaaatc tc                                            22

<210> SEQ ID NO 16
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 16
attcgatcgg ggcggggcga gc                                            22

<210> SEQ ID NO 17
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 17
cgcttgatga gtcagccgga a                                             21

<210> SEQ ID NO 18
<211> LENGTH: 26
<212> TYPE: DNA
<213> ORGANISM: Artificial Sequence
<220> FEATURE:
<223> OTHER INFORMATION: synthetically generated oligonucleotide

<400> SEQUENCE: 18
gatcgaactg accgcccgcg gcccgt                                        26

<210> SEQ ID NO 19
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 19
agttgagggg actttcccag g                                             21

<210> SEQ ID NO 20
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 20
```

-continued

| tgtcgaatgc aaatcactag aa | 22 |

<210> SEQ ID NO 21
<211> LENGTH: 27
<212> TYPE: DNA
<213> ORGANISM: Artificial Sequence
<220> FEATURE:
<223> OTHER INFORMATION: synthetically generated oligonucleotide

<400> SEQUENCE: 21

| agagattgcc tgacgtcaga gagctag | 27 |

<210> SEQ ID NO 22
<211> LENGTH: 10
<212> TYPE: DNA
<213> ORGANISM: Homo sapiens

<400> SEQUENCE: 22

| gctgcgcttg | 10 |

<210> SEQ ID NO 23
<211> LENGTH: 10
<212> TYPE: DNA
<213> ORGANISM: Homo sapiens

<400> SEQUENCE: 23

| ctccccgcag | 10 |

<210> SEQ ID NO 24
<211> LENGTH: 10
<212> TYPE: DNA
<213> ORGANISM: Homo sapiens

<400> SEQUENCE: 24

| cccccaacag | 10 |

<210> SEQ ID NO 25
<211> LENGTH: 10
<212> TYPE: DNA
<213> ORGANISM: Homo sapiens

<400> SEQUENCE: 25

| gaacctcagg | 10 |

<210> SEQ ID NO 26
<211> LENGTH: 10
<212> TYPE: DNA
<213> ORGANISM: Homo sapiens

<400> SEQUENCE: 26

| ttgccactag | 10 |

<210> SEQ ID NO 27
<211> LENGTH: 10
<212> TYPE: DNA
<213> ORGANISM: Homo sapiens

<400> SEQUENCE: 27

| tgcctactag | 10 |

<210> SEQ ID NO 28
<211> LENGTH: 10
<212> TYPE: DNA
<213> ORGANISM: Homo sapiens

```
<400> SEQUENCE: 28
tcctaaatag                                                              10

<210> SEQ ID NO 29
<211> LENGTH: 10
<212> TYPE: DNA
<213> ORGANISM: Homo sapiens

<400> SEQUENCE: 29
tttttctag                                                               10

<210> SEQ ID NO 30
<211> LENGTH: 10
<212> TYPE: DNA
<213> ORGANISM: Homo sapiens

<400> SEQUENCE: 30
tggttcctag                                                              10

<210> SEQ ID NO 31
<211> LENGTH: 10
<212> TYPE: DNA
<213> ORGANISM: Homo sapiens

<400> SEQUENCE: 31
cccttttcag                                                              10

<210> SEQ ID NO 32
<211> LENGTH: 10
<212> TYPE: DNA
<213> ORGANISM: Homo sapiens

<400> SEQUENCE: 32
aaaatcgcgc                                                              10

<210> SEQ ID NO 33
<211> LENGTH: 10
<212> TYPE: DNA
<213> ORGANISM: Homo sapiens

<400> SEQUENCE: 33
ccgccggccc                                                              10

<210> SEQ ID NO 34
<211> LENGTH: 10
<212> TYPE: DNA
<213> ORGANISM: Homo sapiens

<400> SEQUENCE: 34
aaaactaaag                                                              10

<210> SEQ ID NO 35
<211> LENGTH: 10
<212> TYPE: DNA
<213> ORGANISM: Homo sapiens

<400> SEQUENCE: 35
tgacctctcc                                                              10

<210> SEQ ID NO 36
<211> LENGTH: 10
<212> TYPE: DNA
```

```
<213> ORGANISM: Homo sapiens

<400> SEQUENCE: 36
gtggagcgat                                                              10

<210> SEQ ID NO 37
<211> LENGTH: 10
<212> TYPE: DNA
<213> ORGANISM: Homo sapiens

<400> SEQUENCE: 37
ggaatttctc                                                              10

<210> SEQ ID NO 38
<211> LENGTH: 10
<212> TYPE: DNA
<213> ORGANISM: Homo sapiens

<400> SEQUENCE: 38
gtgaacgtgt                                                              10

<210> SEQ ID NO 39
<211> LENGTH: 10
<212> TYPE: DNA
<213> ORGANISM: Homo sapiens

<400> SEQUENCE: 39
ggtttacact                                                              10

<210> SEQ ID NO 40
<211> LENGTH: 10
<212> TYPE: DNA
<213> ORGANISM: Homo sapiens

<400> SEQUENCE: 40
gagttcctca                                                              10

<210> SEQ ID NO 41
<211> LENGTH: 10
<212> TYPE: DNA
<213> ORGANISM: Homo sapiens

<400> SEQUENCE: 41
gttttcagag                                                              10

<210> SEQ ID NO 42
<211> LENGTH: 10
<212> TYPE: DNA
<213> ORGANISM: Homo sapiens

<400> SEQUENCE: 42
ggagaacacg                                                              10

<210> SEQ ID NO 43
<211> LENGTH: 10
<212> TYPE: DNA
<213> ORGANISM: Homo sapiens

<400> SEQUENCE: 43
cacggagccg                                                              10

<210> SEQ ID NO 44
<211> LENGTH: 10
```

```
<212> TYPE: DNA
<213> ORGANISM: Homo sapiens

<400> SEQUENCE: 44
ccgaggaggt                                                          10

<210> SEQ ID NO 45
<211> LENGTH: 10
<212> TYPE: DNA
<213> ORGANISM: Homo sapiens

<400> SEQUENCE: 45
tgaaaacttg                                                          10

<210> SEQ ID NO 46
<211> LENGTH: 10
<212> TYPE: DNA
<213> ORGANISM: Homo sapiens

<400> SEQUENCE: 46
ccaaagaaag                                                          10

<210> SEQ ID NO 47
<211> LENGTH: 10
<212> TYPE: DNA
<213> ORGANISM: Homo sapiens

<400> SEQUENCE: 47
gctacctatg                                                          10

<210> SEQ ID NO 48
<211> LENGTH: 10
<212> TYPE: DNA
<213> ORGANISM: Homo sapiens

<400> SEQUENCE: 48
cagagatgag                                                          10

<210> SEQ ID NO 49
<211> LENGTH: 10
<212> TYPE: DNA
<213> ORGANISM: Homo sapiens

<400> SEQUENCE: 49
gatagaacag                                                          10

<210> SEQ ID NO 50
<211> LENGTH: 10
<212> TYPE: DNA
<213> ORGANISM: Homo sapiens

<400> SEQUENCE: 50
ttttagcaag                                                          10

<210> SEQ ID NO 51
<211> LENGTH: 10
<212> TYPE: DNA
<213> ORGANISM: Homo sapiens

<400> SEQUENCE: 51
gtgagccctc                                                          10

<210> SEQ ID NO 52
```

```
<211> LENGTH: 10
<212> TYPE: DNA
<213> ORGANISM: Homo sapiens

<400> SEQUENCE: 52
gtgagtggcg                                                          10

<210> SEQ ID NO 53
<211> LENGTH: 10
<212> TYPE: DNA
<213> ORGANISM: Homo sapiens

<400> SEQUENCE: 53
aatcggagga                                                          10

<210> SEQ ID NO 54
<211> LENGTH: 10
<212> TYPE: DNA
<213> ORGANISM: Homo sapiens

<400> SEQUENCE: 54
gtgagtttcc                                                          10

<210> SEQ ID NO 55
<211> LENGTH: 10
<212> TYPE: DNA
<213> ORGANISM: Homo sapiens

<400> SEQUENCE: 55
gtgagtattc                                                          10

<210> SEQ ID NO 56
<211> LENGTH: 10
<212> TYPE: DNA
<213> ORGANISM: Homo sapiens

<400> SEQUENCE: 56
gtaaggagac                                                          10

<210> SEQ ID NO 57
<211> LENGTH: 10
<212> TYPE: DNA
<213> ORGANISM: Homo sapiens

<400> SEQUENCE: 57
gtgagtgtaa                                                          10

<210> SEQ ID NO 58
<211> LENGTH: 10
<212> TYPE: DNA
<213> ORGANISM: Homo sapiens

<400> SEQUENCE: 58
gtaaagtggg                                                          10

<210> SEQ ID NO 59
<211> LENGTH: 10
<212> TYPE: DNA
<213> ORGANISM: Homo sapiens

<400> SEQUENCE: 59
gtaaagtatt                                                          10
```

HUMAN RIBONUCLEOTIDE REDUCTASE M2 SUBUNIT

RELATED APPLICATION

This application claims priority to U.S. Provisional Application Serial No. 60/368,685, filed Mar. 29, 2002, the content of which is incorporated herein by reference.

FEDERALLY SPONSORED RESEARCH OR DEVELOPMENT

This application was funded in part by NIH Grants CA72767. The U.S. government has certain rights in this application.

BACKGROUND

Ribonucleotide reductase is a highly regulated enzyme involved in the DNA synthesis pathway. It is responsible for the de novo conversion of ribonucleoside diphosphates to deoxyribonucleoside diphosphates that are essential for DNA synthesis and repair (Cory and Sato, (1983) Mol Cell Biochem 53, 257–266; and Thelander and Berg (1986) Mol Cell Biol 6, 3433–3442). Ribonucleotide reductase consists of two subunits, M1 and M2. M1 is a 170 kDa dimer required for enzyme regulation (Chang and Cheng (1979) Cancer Res 39, 5081–5086). M2 is an 88 kDa dimer containing a tyrosine free radical and a non-heme iron.

SUMMARY

The invention relates to a newly isolated genomic sequence of the human ribonucleotide reductase M2 subunit (hRRM2) gene. The 10.3 kb sequence (SEQ ID NO:1 shown below) was deposited in GenBank (Accession Number AY032750).

```
                                                          (SEQ ID NO:1)
   1 CCCCGAGCCG CGGTTTCTCC ACCCTAATGG TGAACAGCCT TTTGGAAGTC GCGCTAACCT

61 TGGCCTGAGA CCTGCAAACT TGCCCAGGCT GGGGCGTGTG AACCGGCGAG CGCGCAGCGG

121 AAACGGGGCG GGGCACCTGA GGCTGGGAAT GCAGAGGAGC CTTCCGGGGG GCGGGCGGG

181 GCCTCCCGTG CATACCAATG GTGGGGTAGA TTCAAATGTC AATTCGCGCG CTCAAGTGGC

241 TTCCGCCAGG AATCCCGACC CTTATGGAAG CGGAAGGAAG ATCGCTTGAT ACCAACCTGG

301 GCTAGCTAGC GAGACCTCGT CTGTTTACTT AAATAAAACC AAAAAAACGA GCACCGAGGG

361 AAAAAGGAGT GAATCCCGGG GCTAGCAGCA GCCTGCGGCG GGCGCTCTCC CGGGAGTGGC

421 TGCACCGCCC GACCTCCCCG GAGGCGGAAC CGCCCGCATT GCCGCGTGGC CCTGGGCGCC

481 GCCACCTCCT CCGCAGCGGG GCAAAGTTGC CGGACCTGGG GGCAGGAGGG CCACGCCGAG

541 ATGACTCAGG TTTAGCGCGG GAGGGGAGGA TGGCGACTTC ACCCGGCCTT TAACAACACG

601 TACGCATCTT TCGGCGTCTT CTACAATGGC TATGTTAATT ACGTGGCCAG GAACTAAACT

661 ATCAATGAAG CCACCTCTGA CTACTTCAGT TACAGTGAGT TTAACAGGAG CAAAAAAGCA

721 CGTGGCGCCC TAGGGCAACC GAAACGAGGG TTTTAGACGC TGATTATGGG AAATTGAAAT

781 CTGAGTTGAG TATGAGATGA CACCAATAAA TTATAATTTT GTTAGATAAT AGCTTTATCA

841 GCCATAAAGT AATCAATAAA AATACCAGTT TCCTGGAGAT GGATGCTTTA GTGTGTTTGG

901 GGTGAAAATG GCGATGAATG GCGAGTTGCT TTAAACAAAT CATGGTACAC CAAAGTTTTA

961 GTTGTGGCTT TGTGTAAGGA ATGTGATGGG CACTTATTCC TGCAACACGA GAATACTATG

1021 ATTTACAAGT CCGTAGTACT TTTAAGAAAT GAGAGAAACA GACCTAGGTG GGGAGGGTAC

1081 CTGTCCCACC CCACCCTCTT TAAAGTATCT TATCTAGAAA AGGCTTTGTG AAAAAAAAAG

1141 TCCCGGGTCT CTCTCAATAA CAGCCCTGAG CGCAGCTGTT GAAGCTTTCT CAGGTTAATG

1201 ATTTCTTTCT TGGATCTTAA AGTTTCTTTC TCTTCCTTTA TTTTTGGCAT TTTGCCCGTT

1261 GCAGGGCCTG GCAAATCAGA AAGCCACATA GAAAATTAAA TGAAAGCTAT TGCTAAGTTC

1321 CAGTCTCTAC ACCAGTGGAG TTTTCAAACT CCTCTTCAGC ATATTTGACG CCCAATGAGT

1381 AGTACATTAA TTCCTAGTCC TAAAATCATT CTGTGAACTT TCTCCCAGGA ATTTTTGCTC

1441 AGTTTGCAAT TAAAACAACT TTTTTTCTTC TCTTTTTAAT GGCAGAGGCG GGGTCTCACT

1501 ATGTTGCCCA GGATGGTCTC CAGCTCCTGG CCTCAAACAA TCCTCCTGCC TTGGCCTCCC

1561 AAAGTGCTGG GATTACAGGC GTGAGCCACC GCGCCCAGCC ACAGTTTGCA ATTCTTAAGG
```

-continued

```
1621 CAAGGGTGAC AATAGGGGTC AGGGGTCTGA CAGGAGACAG GATTTCTGTG GAAAACTGCA
1681 CCAAGGGCCT TCTCGCCATG TCCCGTAGTT TGAAGGTTTA CAAAGGACTG CACATTTTAC
1741 ATGAGTCATC TCAACGAACG CTCTCCTCAC CGCATTAACA GTCCACGCGG TTACGAGTCC
1801 CATTTTACTC ACGGGGACAC CGAATCTGTA AGAAGCCTGG TCGCTTGTCC CAGCAAAACG
1861 AGCCACGGGG CTCAGCGGCC CTAACTTTTA GGCTGTAGGG TCCTCGCCGA CCACCCCGCC
1921 AAAATGTCAG GCCTCGGGGC CCTTGCACCC CCACCGCAGG GACACGGATC GAAAGGGTCG
1981 CAGCAACGCC TCCCCCGCAC CCAGGAGCGT TTTCCAGGCC TTTGCACCAA CCTCGTTGGC
2041 TAAGCCCCCT GCCCGGCGGC GGCCCGGCTG GGAGGAGGTG CTTTCGGGAG GCGGGGCCGC
2101 GGCCCGGGGA TCCTCTCGCG CCCGCGGGCT CCAATCGCTG CTCCTCACGC AATCCTAAAC
2161 GGTTCCCGGG CGAACCGGGG CCCGCGCGCG CCAAGGCCGC CGAGACCCTC AGGGGCTGCG
2221 GCCCTGGTCC CGCGGGACCT GTGGGGGCCT GGGCGGCGGC GCCCCGACC CAGCCAGCGG
2281 ACGGGCCGGG GGGGAACCG GGAGGTCCCG GGGGGCGTCC ACGGGGTGT CCCCGGGGGT
2341 CTCCGGAAGG CGCCGGCGGA GGCTCCCGCG CTGCGCTTGA AAATCGCGCG CGGCCCCGCG
2401 GCCAGCCTGG GTAGGGGCAA GGCGCAGCCA ATGGGAAGGG TCGGAGGCAT GGCACAGCCA
2461 ATGGGAAGGG CCGGGCACC AAAGCCAATG GGAAGGGCCG GGAGCGCGCG GCGCGGGAGA
2521 TTTAAAGGCT GCTGGAGTGA GGGGTCGCCC GTGCACCCTG TCCCAGCCGT CCTGTCCTGG
2581 CTGCTCGCTC TGCTTCGCTG CGCCGCCACT ATGCTCTCCC TCCGTGTCCC GCTCGCGCCC
2641 ATCACGGACC CGCAGCAGCT GCAGCTCTCG CCGCTGAAGG GGCTCAGCTT GGTCGACAAG
2701 GAGAACACGG TGAGCCCGCG GGGAGGGCGC TGCGGGCAGG GGAGGGAGGC AGGGAAAGCG
2761 AAGCCGCTCC TCACTCACAC GCGTCTCCCC GCAGCCGCCG GCCCTGAGCG GGACCCGCGT
2821 CCTGGCCAGC AAGACCGCGA GGAGGATCTT CCAGGAGCCC ACGGAGCCGG TGAGTGGCGG
2881 GCGTGGGCA GAGGGGCCAG GGACGGCCTT GGGCGTCTTG GCGCCAAAGC CGCATTGTTT
2941 CCTCAGCTGT TCACACTCCC GCCCCGGCTC CTTTCCCGCC TAGGCGGCCC CTCCCCAGGG
3001 CTGCCTCCCG CGCCCCTCGG CCCATTTCCC GGTTCGGCG TGCGCTCCTC TGCTGCGACC
3061 CACGGAGTGC GACGGGACAG CCACGTTTTC ACATCGGGCC CCGTGAAATT GCCGCCAATG
3121 GAAAGGACTT GGTCCAGAAA AACGTTAGTT TCATATGGTT CGCCCGGTAC TTAAATGTTT
3181 TATTTTCTCC CCCAACAGAA AACTAAAGCA GCTGCCCCCG GCGTGGAGGA TGAGCCGCTG
3241 CTGAGAGAAA ACCCCCGCCG CTTTGTCATC TTCCCCATCG AGTACCATGA TATCTGGCAG
3301 ATGTATAAGA AGGCAGAGGC TTCCTTTTGG ACCGCCGAGG AGGTAATCGG AGGACCCCAG
3361 AAGACCCCTG CAGGGGTGAC CGTCACGCCT CAGACATAAA TGCACTTGGA GGTTCCCGTT
3421 GGCAAGGGGG GCTAACTGTG GGGCATAGTA AGTGGTGCCA GCATACTTAA AGTTTGAGTG
3481 CTCAGTGTGA GTCCTGTAGG CTTTACTCTC TTCCTTTTAT GCTAAAATTG TGACTTCCGA
3541 ACCTCAGGTG ACCTCTCCAA GGACATTCAG CACTGGGAAT CCCTGAAACC CGAGGAGAGA
3601 TATTTTATAT CCCATGTTCT GGCTTTCTTT GCAGCAAGCG ATGGCATAGT AAATGAAAAC
3661 TTGGTGAGTT TCCAAAACAT CTTTCATTCA TTTGACGTTG ACGATCTGAG GTCGAACTAG
3721 TTCGCTTTCC TCGTCTTGTA CGTTTTTCCA TGCTGAGTGC ATCTGTGTGT GTAAGCTGGG
3781 TTTTATATTA CATGGCATTT CCTGTTTTGT AACACTTTGC AGTTCTTTCT TATGGTATTT
3841 TCCCGACTCT AGAGAAGCTG AGACAATATT AAGTGGTAGC AATGTGATGA CTCTTTGTGG
3901 CCACCACATC TGCCCCCTCT TTTTTTTTTT TTTTTGAGAC AGAGTCTCAC TCTGGCCCAG
3961 GCTGGAGTGC AGTGGCGTGA TCTTGGCTCA CTGCAACCTC CGCCTCCTGG GTTCAAGCGA
```

-continued

```
4021 TTCCCCAACC TCAGCCTCAT GAGTACCTGG GATTACAGAC GTGCGCCACC ATGCCTAGCT

4081 AATATCTGTA TTTTTAGTAG AGACAGGGTT TTACCATGTT GGCCAGGCTG GTCTCGAACT

4141 GCTGACCTCA GGTGATCCAC CCACCTTGGC CTCCCAAAGT GTTGGGATTA CAGGCGTGAG

4201 CCACCACGCC CGGCTCTGCT CCCTCCTTTT TGTGGCTTTG CTGTTTTAAT AATAATTTGG

4261 TTGTATCTCT TATTGCGAAT GGATCTTTCT TGACATAAAT TAATTAGGAA ATCGAGCGCT

4321 CACAAATCCT ATTTTATATG TATCTATTTC CTGATATGTA AGTTGAGCAT ATGACATAAA

4381 ATATCAAAGA ACTGTGACAA ATTGGATGAA ATATATATAG AAATAAACCT TATAATGGTA

4441 CAAAGAGTGC GATGCTGCCA GTATCCGTTG ACAGTTGCTG CTGTTGGTTT TTTCTCAAGC

4501 TTAACTTTGA TGTGTTTTGC CACTAGGTGG AGCGATTTAG CCAAGAAGTT CAGATTACAG

4561 AAGCCCGCTG TTTCTATGGC TTCCAAATTG CCATGGAAAA CATACATTCT GAAATGTATA

4621 GTCTTCTTAT TGACACTTAC ATAAAAGATC CCAAAGAAAG GTGAGTATTC AAGTGGTATG

4681 CCAAGATTTT TAGGACTCAC TAATTGTTGA TTTATTCAC ATTTTTAGTT CACCTAGGGA

4741 TAAAAATGAC TCCAGAATGA CTAAGACAGT CATAGGCATT CCCAGCACCC GTGGTCATGT

4801 CTGCTCTTAG CAAGGGGCCT AAATGCACTT TATTATTCAC TTAGAGTTGT GAAGGTACTC

4861 CTTTTAAAGT TGGATGTCTA CCAATGTAAA ACCTTCTTTT GAAAAAATTC CTAGATGTTG

4921 GGTAAGACAA ACTAAAACCT ATGTCTGACC ATCTTTGCTC ATTTGGTAAA GTTGTTGAGA

4981 AGCTAGAATG TGGGGCTGCA GTGGGATGGA CGGGGAAGGA CTTGCCTCCT AAGAAGCCTG

5041 CAGTATAGTA TAGGCAAATA AGACTTAGTA GGAGTTACAT AAGGCAGAGG CAGCAGTGAA

5101 CCCTGAGACT GATTTAGGCA TGCAGGAGTT TGGCTGAATA AAGGTAGCTT AAGGTCTGTT

5161 TTGTTTTGGA GATTGGAGGT GGGGGGATTA GAAATGGGCT GCTGGAGTAG TCTAGATACA

5221 AAGGTCAGCT TTAGGGTGGC GCGCGGTGGT TCTCGCCTGT AATCCCAGCA CTTTGGGAGG

5281 CTGAAGCGGG CGGACAATGA GGTCAGGAGA TCGAGACCAT CCTGGCTAAC ACGGTGAAAC

5341 CCCGTCTCTA CTAAAAATAA AAAAAGTGGT GGCGGGCGCC TGTAGTCCCA GCTGCTTGGG

5401 AGGCTGAGAC AGGAGAATGG CGTGAACCCG GGAGGCGGAG CTTGCGCTCC AGCCTGGGTG

5461 ACAGAGCAAG ACTCCGTCTC AAAAAGCAAA ACAAAACAAA AAAAACAAAG GTCAGCTTTG

5521 GGGACCAGAA CCTTGTATGG AGTGGAAGTG GTGAAGCTGC AACCTAAAGT AGCCGTTGTA

5581 GACTTTGAAG TACATGAAGA GGAAAAGTGG TAACTTGAAA GGACTGAGGA AACATTGGGA

5641 GTAAAGAGAT TTGAACATGT TTATAGGTGG AAATTGAGAA AAGAAGGCAA AGATTAGGGG

5701 TACGATCGGG GGCAAATGCC CAGAAGGGGA ACAGGAAGGT CTGCTGGGGA AGCCTCAAAA

5761 ACAAGGGAGA GGCAGACCCA GGTCTCAGAG AGAGGGACAG TGAGATGGAA AGAATGAACG

5821 ACAGCTGGGC ATGGTAGTCT GAGCTAGTAG TCCCAGCTAC TTGGCAGGCT GAGGCAGAAG

5881 GATGGCTTGA GCCCTGGAGT TTGGTTTTAC CGTGAGCTGT GATCATCTCG CTGCACTCTA

5941 GCCTGGGCAA CAGAGTGAGA CCCTCATCTC TTTAAAAAAA AAAAAAAAAA AAAAAAAAA

6001 GGGTCTGGTG CCCTTGGCTT CAGAACACAA AGTCATCTGG GTAGGAACAG TCTGGGAAAT

6061 GAGTAGCCTC TCAAGGTGGG CACCAGAATA AAGGGAGGCA GAGGAGGGTG GTAAGGGAGA

6121 TCCAGTTAAC TGTAGTACCC ATGGATTTGC TTTCCTGACC TGGGATCGAC AGTGTAGCAC

6181 AGAGTCACTA GTAGGAAGCA ATCTTAGTTT ATTGGTTTAA TTATTTTATG ATATAGATGT

6241 GGCAACTGAG GCCAAATAAT GCACCTAATC ATAGTCTGAT AATAGCACAG CAGTTAGGAT

6301 TTTATGGTTC TTCAAATTTA AATTCTATGA TTCTTCAAAT TGAACAATGA TCTGGACTTG

6361 AAATAATTTT AAAGGCAACA AATGTCCCTG CTGTACTGGA CTATGTTTTA CTGTCTGTAG
```

-continued

```
6421 ACCCTGAAGC TCAATATGAA CTACAGAATA CCCAAACTTG TATTAATGTA AATCAAGTGT
6481 TGAGGTTTTT AAAAGAACAC TGGAGGGAAA AACTGACCAG TAAAAATAAA ACATTTCGGT
6541 GTGAGTTCTT CCTTTAGGAA GAGGATTGGC AAATACTTGA ATTTGGCCTT TGTCCCACTT
6601 ATCTAGCAGT TGGTAATCGG AGGTCTTTTA CTGTAATGCT TCAATTGCTG ATACCGTATG
6661 TGCCTACTAG GGAATTTCTC TTCAATGCCA TTGAAACGAT GCCTTGTGTC AAGAAGAAGG
6721 CAGACTGGGC CTTGCGCTGG ATTGGGGACA AAGAGGCTAC CTATGGTAAG GAGACCCTTG
6781 CCCCTACTTA AACCTGAGCT TCATTTTCCA AGTAATGTTA CTGGATTTTT GGCCCTTGAA
6841 TACCAACTCA CTAGAATCAT GTTGGTGTTT AACTCCTAAA TAGGTGAACG TGTTGTAGCC
6901 TTTGCTGCAG TGGAAGGCAT TTTCTTTTCC GGTTCTTTTG CGTCGATATT CTGGCTCAAG
6961 AAACGAGGAC TGATGCCTGG CCTCACATTT TCTAATGAAC TTATTAGCAG AGATGAGGTG
7021 AGTCTAAGTC AAATAATAGG GTGACCTAAA CCCCAAACAC AACTTTAATG TGTGAGTTCA
7081 TTCACTGACG GGACCTGAG ATGCTAGATG GCATATATCC ACATTTAATG TGTGAGTTCA
7141 ACCATACACA TACTTGACAA AAGAAGGAAA TACTTTCATT TACTGAAACT GTTTTACTTG
7201 CATTCTCAAT ATATTGTAAT ACATTTGTAC ATATGTATTC CCTATAGGC TTTGAATGCA
7261 TAAAACTACA AGTTCTTTGT TTTTTGAGGT GACGGAATCT TGCTCTGTCG TTCCAGGCTG
7321 GAGTGCAATG GCGTGATCTT GGCTCACTGC AACCTCTGCC TCCTAGGTTC AAGTGATTCT
7381 CCCGCCTCAG CCTCCCAAGT AGCTGGGATT GTAGGTGCCT GCCACCATGC CCAGCTAATT
7441 TTCGTCTTTT TATACAGACG GGGTTTCACC ATGTTTGCCA GACTGGGGTT GAACTCCTGA
7501 CCTCAGGTGA TCAGGTGATC CACCCGCCTC GGCCTCCCAG AGTGCTGGGA TTATAGGCAT
7561 GAGCCACCAT GCCCAGCCAA AACTACAAGT TATTGATGGG ATTGGGATTT TAAGGGATGT
7621 TTTATTATTT TTGCCTGGTA TTAATATGTT ATCCCTTTTT CCGTAAAAAT GTTCATAGTA
7681 GAGCCAGGAG CGGTGGCTCA TGCCTGTAAT CCCAGCACTT TGGTAGGCCG AGGCGGGTGG
7741 ATCATGAGGT CAGGAGATTG AGACCATCCT GGCTAACACG GTGAAACCCC ATCTCTACTA
7801 AAATTACAAC AAAATTAGCC GGGTATGGTG GACGTGCCTA TTGTCCCAGC TACTTGAGAG
7861 GCTGACGTAG GAGAATCGCC TGAAACCTGG AAAGTGGAAG GTTTGCAGTG GAGTCCGAGA
7921 TCACAACACA CTGCACTCCA GCCTGGGTGA CAGTCCCCCC GAAAAAGAAT GTTCATAGTA
7981 GCCATTATGT TTCTCCTGTT TGATCTAGAA ATTGCCCCTC TACTTCAATA TTAATAAGCA
8041 TTTCAATGAA ATGAGTATAC ATTTTGGTCT AGTGTATGTC TTTGATTAAG TCACATTTGA
8101 AAAGCCAGGA GCATGAACTC CATCTTACTT GGAGCCCAGT GGGCAAATCA AATATGGTTA
8161 CCTTGTAGGA GGGCTTCCTT ACTGGATTGG GAGATAAGCT GTGAAGCTTG ATGTTTAATG
8221 CAGTAACTTG CAAACTTGAT TTACTTGAAA TTGCATACAA TTTCCTGAGC ATCTAAAAAC
8281 TAGCTTATTA CTGAGCTTTG CCTTTTCCTG CTGGGAGTAG TGGCAAAATT AGCACTCATG
8341 GCTGTAGAAA GATCACTGAG TGAAGCTCTG ACTCCTCCTT TGCCAAACAC ACAGCAGAGC
8401 AAGAAATACA CCTTGCCTGT CTTCATCTAG GTGGCAACTT TGAGGGTCTT GAATGGGACT
8461 GAGCTTGCCT TGGTGGTGAC ATCAGCAGAG AAGTCAGTAG TTGAAGTCAT CTTCCCTTTG
8521 AGAGTTCAAG TGCTCTCAGT ATGGCTGAGC ATGTTGGATA GGAGAATGC AGAAAAGGAC
8581 AAAGTAATTT CATATTACCA TGTTAATGAC AGAAGTCTTC TGGCTTTAGT GATCTTGAAC
8641 TTTTTTTTCT AGGGTTTACA CTGTGATTTT GCTTGCCTGA TGTTCAAACA CCTGGTACAC
8701 AAACCATCGG AGGAGAGAGT AAGAGAAATA ATTATCAATG CTGTTCGGAT AGAACAGGTA
8761 AAGTGGGTGA TGAAATGGGT CACTCAAGCT TGCTAGAAAA TGCCTGTGCT TTAGTTGTAT
```

```
-continued
 8821 TCAGAAGCTG TATTTTGGTT CCTAGGAGTT CCTCACTGAG GCCTTGCCTG TGAAGCTCAT

8881 TGGGATGAAT TGCACTCTAA TGAAGCAATA CATTGAGTTT GTGGCAGACA GACTTATGCT

8941 GGAACTGGGT TTTAGCAAGG TAAAGTATTG TTTACATAGC CTTTTGCTTG TTTTGAAGCT

9001 GGTGCTCTGT ATTTATATCT TGATGTGAAC CCTTTTCAGG TTTTCAGAGT AGAGAACCCA

9061 TTTGACTTTA TGGAGAATAT TTCACTGGAA GGAAAGACTA ACTTCTTTGA GAAGAGAGTA

9121 GGCGAGTATC AGAGGATGGG AGTGATGTCA AGTCCAACAG AGAATTCTTT TACCTTGGAT

9181 GCTGACTTCT AAATGAACTG AAGATGTGCC CTTACTTGGC TGATTTTTTT TTTCCATCTC

9241 ATAAGAAAAA TCAGCTGAAG TGTTACCAAC TAGCCACACC ATGAATTGTC CGTAATGTTC

9301 ATTAACAGCA TCTTTAAAAC TGTGTAGCTA CCTCACAACC AGTCCTGTCT GTTTATAGTG

9361 CTGGTAGTAT CACCTTTTGC CAGAAGGCCT GGCTGGCTGT GACTTACCAT AGCAGTGACA

9421 ATGGCAGTCT TGGCTTTAAA GTGAGGGGTG ACCCTTTAGT GAGCTTAGCA GAGCGGGATT

9481 AAACAGTCCT TTAACCAGCA CAGCCAGTTA AAAGATGCAG CCTCACTGCT TCAACGCAGA

9541 TTTTAATGTT TACTTAAATA TAAACCTGGC ACTTTACAAA CAAATAAACA TTGTTTTGTA

9901 TGTGGGATAA AGGAATCTCT CAGGGCAAGG AGCTTCTTAA GTTAAATCAC TAGAAATTTA

9961 GGGGTGATCT GGGCCTTCAT ATGTGTGAGA AGCCGTTTCA TTTTATTTCT CACTGTATTT

10021 TCCTCAACGT CTGGTTGATG AGAAAAAATT CTTGAAGAGT TTTCATATGT GGGAGCTAAG

10081 GTAGTATTGT AAAATTTCAA GTCATCCTTA AACAAAATGA TCCACCTAAG ATCTTGCCCC

10141 TGTTAAGTGG TGAAATCAAC TAGAGGTGGT TCCTACAAGT TGTTCATTCT AGTTTTGTTT

10201 GGTGTAAGTA GGTTGTGTGA GTTAATTCAT TTATATTTAC TATGTCTGTT AAATCAGAAA

10261 TTTTTTATTA TCTATGTTCT TCTAGATTTT ACCTGTAGTT CATT
```

The hRRM2 gene was found to consist of 10 exons. Two transcription initiation sites were identified, corresponding to mRNA transcripts of 3.4 kb and 1.65 kb, respectively. Deletion analysis of the 5'-flanking region showed that the promoter activity is consistent with the presence of two separate promoters driving expression of the two hRRM2 transcripts: one is located between bp 1908–2310 of SEQ ID NO:1 and designated SEQ ID NO:2; the other is located between bp 2366–2567 of SEQ ID NO:1 and designated SEQ ID NO:3. The composite promoter (bp 1908–2567 of SEQ ID NO:1) is designated SEQ ID NO:4. As shown below, the promoter region of hRRM2 contains many binding sites for transcriptional factors. Thus, these promoters are useful for fine-tuned regulation of gene expression.

Accordingly, the invention features an isolated nucleic acid containing a promoter sequence at least 60% (including any percentage between 60% and 100%, e.g., 70%, 80%, 90%, 95%, or 100%) identical to SEQ ID NO:2, 3, or 4 and a nucleotide sequence encoding a transcript. The promoter sequence is operably linked to the nucleotide sequence, i.e., transcription of the nucleotide sequence is under the control of the promoter.

An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

The "percent identity" of two nucleic acid sequences is determined using the algorithm of Karlin and Altschul ((1990) Proc Natl Acad Sci USA 87, 2264–2268), modified as in Karlin and Altschul ((1993) Proc Natl Acad Sci USA 90, 5873–5877). Such an algorithm is incorporated into the XBLAST programs of Altschul et al. ((1990) J Mol Biol 215, 403–410). BLAST nucleic acid searches are performed with the XBLAST program. Where gaps exist between two sequences, Gapped BLAST is utilized as described in Altschul et al. ((1997) Nucleic Acids Res 25, 3389–3402). When utilizing BLAST and Gapped BLAST programs, the default parameters of the respective programs (e.g., XBLAST) are used. See the World Wide Wed address ncbi.nlm.nih.gov.

The invention also features an isolated nucleic acid at least 86% (including any percentage between 86% and 100%, e.g., 90%, 95%, or 100%) identical to SEQ ID NO:1, which can be used, e.g., for detection of amplified RRM2 gene in a subject, or screening of therapeutic compounds for treating a cell proliferation-associated disorder.

It was discovered that the hRRM2 gene is amplified in gemcitabine-resistant or hydroxyurea-resistant human nasopharyngeal cancer (KB) cells. Consequently, the invention features a method of determining whether a subject is suffering from or at risk for developing a cell proliferation-associated disorder (e.g., cancer). The method involves providing a test sample (e.g., a tissue sample or a body fluid sample) containing genomic DNA from a subject, and determining the level of RRM2 genomic DNA in the test sample, e.g., by Southern blot analysis. If the level of RRM2 genomic DNA in the test sample is higher than that in a normal sample, it indicates that the subject is suffering from or at risk for developing a cell proliferation-associated disorder.

The invention further features a method of identifying a compound for treating a cell proliferation-associated disorder. In one example, the method involves contacting a compound with a cell containing amplified RRM2 genomic DNA, and determining the level of RRM2 genomic DNA. If the level of RRM2 genomic DNA in the presence of the compound is lower than that in the absence of the compound, it indicates that the compound is a candidate for treating a cell proliferation-associated disorder.

In another example, the method involves contacting a compound with a system (e.g., a cell system or a cell-free system) containing a nucleic acid that includes a marker nucleotide sequence operably linked to a promoter sequence of SEQ ID NO:2, 3, or 4, and determining the expression level of the marker nucleotide sequence. If the expression level of the marker nucleotide sequence in the presence of the compound is different from that in the absence of the compound, it indicates that the compound is a candidate for treating a cell proliferation-associated disorder. The marker nucleotide sequence can be, e.g., the coding region of the hRRM2 gene, or any of other suitable genes. Expression of the marker nucleotide sequence can be determined, e.g., by using Northern blot analysis of the transcript, Western blot analysis of the protein, or activity assays of the protein. The system can include a nucleic acid encoding various transcriptional factors interacting with SEQ ID NO:2, 3, or 4, e.g., SP1, c-Ets, MZF1, E2F, Lyf-1, GATA-X, HSF2, AP-1, CdxA, IK-2, Sox-5, SRY, Brn-2, HNF-1, STATx, GATA-1, USF, Pbx-1, Oct-1, GATA-2, CRE-Bp, or Nkx-2. Alternatively, the system can contain one or more of these factors themselves.

In yet another example, the method involves contacting a compound with a cell containing amplified RRM2 genomic DNA and expressing the ribonucleotide reductase MI subunit (RRM1) or p53R2 gene, and determining the level of RRM1 or p53R2 mRNA or protein in the cell. If the level of RRM1 or p53R2 mRNA or protein in the presence of the compound is lower than that in the absence of the compound, it indicates that the compound is a candidate for treating a cell proliferation-associated disorder.

In still another example, the method involves contacting a compound with a cell containing amplified RRM2 genomic DNA and expressing RRM1 and p53R2 genes, and determining the level of RRM1 and RRM2 or RRM1 and p53R2 interaction in the cell. If the level of RRM1 and RRM2 or RRM1 and p53R2 interaction in the presence of the compound is lower than that in the absence of the compound, it indicates that the compound is a candidate for treating a cell proliferation-associated disorder.

Also within the scope of the invention is a method of treating a cell proliferation-associated disorder in a subject whose RRM2 genomic DNA is amplified. The method involves administering to the subject an effective amount of a compound that reduces the level of RRM2 genomic DNA, transcription from a promoter sequence of SEQ ID NO:2, 3, or 4, RRM1 mRNA or protein, RRM2 mRNA or protein, p53R2 mRNA or protein, RRM1 and RRM2 interaction, or RRM1 and p53R2 interaction in the subject. For example, the level of RRM1, RRM2, or p53R2 protein can be reduced by using an antibody to RRM1, RRM2, or p53R2, respectively. Similarly, the interaction between RRM1 and RRM2 can be reduced by using an antibody to RRM1 or RRM2, whereas the interaction between RRM1 and p53R2 can be reduced by using an antibody to RRM1 or p53R2. The interaction between RRM1 and RRM2 or RRM1 and p53R2 can also be inhibited by using a competitor peptide or polypeptide such as a 7-amino acid peptide FTLDADF (SEQ ID NO:5).

A cell proliferation-associated disorder in a subject whose RRM2 genomic DNA is amplified can also be treated by administering to the subject an effective amount of an RRM2 inhibitor (e.g., hydroxyurea) followed by administering to the subject an effective amount of a nucleotide or nucleoside analog (e.g., gemcitabine).

Moreover, the invention features a method of developing a procedure for treating a cell proliferation-associated disorder in a subject, e.g., a subject who has amplified RRM2 genomic DNA. The method involves providing a plurality of subjects suffering from a cell proliferation-associated disorder; administering to each subject an effective amount of an RRM2 inhibitor; administering to each subject an effective amount of a nucleotide or nucleoside analog following administration of the RRM2 inhibitor, each at a unique time point; and selecting an optimal time point at which the cell proliferation-associated disorder is inhibited to the greatest extent.

The details of one or more embodiments of the invention are set forth in the accompanying description below. Other features, objects, and advantages of the invention will be apparent from the detailed description, and from the claims.

DETAILED DESCRIPTION

The invention is based on the identification of genomic sequence of the human ribonucleotide reductase M2 subunit gene and the unexpected discovery that this sequence is amplified in drug-resistant cancer cells. Further, it was found that low-dose hydroxyurea (HU, an S-phase specific inhibitor of ribonucleotide reductase with a broad spectrum of anti-tumor effects) enhanced the activity of gemcitabine (Gem, a deoxycytidine analogue whose active metabolite, dFdCTP, blocks DNA elongation and has a cytotoxic effect) in a time and sequence dependent manner. Unexpectedly, this enhancement is associated with a decrease in hRRM2 mRNA, protein, or activity. Moreover, a phase I trial demonstrated that hydroxyurea followed by gemcitabine can be safely administered to human patients and has cytotoxic effect on cancer cells.

In one aspect, the invention features an isolated nucleic acid containing a promoter sequence at least 60% identical to SEQ ID NO:2, 3, or 4 and a nucleotide sequence operably linked to the promoter sequence and encoding a transcript. Expression of the nucleotide sequence is directed by the promoter sequence.

In another aspect, the invention features an isolated nucleic acid at least 86% identical to SEQ ID NO:1. This nucleic acid is useful, e.g., for diagnosing a cell proliferation-associated disorder, or identifying a compound for treating such a disorder.

A nucleic acid of the invention can be expressed in vitro by DNA transfer into a suitable host cell by methods known in the art. For example, the nucleic acid can be inserted into a recombinant expression vector. A variety of host-expression vector systems can be utilized to express a nucleic acid of the invention. These include, but are not limited to, microorganisms such as bacteria transformed with recombinant bacteriophage DNA, plasmid DNA, or cosmid DNA expression vectors; yeast transformed with recombinant yeast expression vectors; and human cell lines infected with recombinant virus or plasmid expression vectors. Isolation and purification of recombinant polypeptides, or fragments thereof, can be carried out by conventional means including preparative chromatography and immunological separations involving monoclonal or polyclonal antibodies.

The invention also features methods for diagnosing and treating a cell proliferation-associated disorder, and identifying therapeutic compounds for treating such a disorder.

A diagnostic method of the invention involves comparing the RRM2 genomic DNA level in a sample prepared from a subject (i.e., an animal or a human) with that in a sample prepared from a normal subject, i.e., a subject who does not suffer from or at risk for developing a cell proliferation-associated disorder. A higher RRM2 genomic DNA level indicates that the subject is suffering from or at risk for a cell proliferation-associated disorder. This method can be used on its own or in conjunction with other procedures to diagnose a cell proliferation-associated disorder in appropriate subjects.

Amplification of a gene locus can be detected by a variety of methods known in the art. For example, the copy number of a gene locus can be determined and compared by PCR amplification of genomic DNA prepared from a test sample and a control sample. Amplification of a gene locus can also be identified by Southern blot analysis. Fluorescence in situ hybridization (FISH) of a DNA sequence to a metaphase chromosomal spread can further be used to provide a precise chromosomal location and an amount of the DNA sequence present in the chromosome.

The invention also provides a method for identifying and manufacturing compounds (e.g., proteins, peptides, peptidomimetics, peptoids, antibodies, or small molecules) that decrease the RRM2 genomic DNA level, modulate expression of a marker nucleotide sequence under the control of a promoter sequence of SEQ ID NO:1, 2, or 3, decrease the level of RRM1 or p53R2 mRNA or protein, decrease the level of RRM1 and RRM2 interaction, or decrease the level of RRM1 and p53R2 interaction in a system (a cell system or a cell-free system). Compounds thus identified can be used, e.g., for preventing and treating a cell proliferation-associated disorder.

The candidate compounds of the invention can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation); spatially addressable parallel solid phase or solution phase libraries; synthetic libraries obtained by deconvolution or affinity chromatography selection; and the "one-bead one-compound" libraries. See, e.g., Zuckernann et al. (1994) J Med Chem 37, 2678–85; and Lam (1997) Anticancer Drug Des 12, 145.

Examples of methods for the synthesis of molecular libraries can be found in the art, for example, in: DeWitt et al. (1993) PNAS USA 90, 6909; Erb et al. (1994) PNAS USA 91, 11422; Zuckermann et al. (1994) J Med Chem 37, 2678; Cho et al. (1993) Science 261, 1303; Carrell et al. (1994) Angew Chem Int Ed Engl 33, 2059; Carell et al. (1994) Angew Chem Int Ed Engl 33, 2061; and Gallop et al. (1994) J Med Chem 37,1233.

Libraries of compounds may be presented in solution (e.g., Houghten (1992) Biotechniques 13, 412–421), or on beads (Lam (1991) Nature 354, 82–84), chips (Fodor (1993) Nature 364, 555–556), bacteria (U.S. Pat. No. 5,223,409), spores (U.S. Pat. No. 5,223,409), plasmids (Cull et al. (1992) PNAS USA 89, 1865–1869), or phages (Scott and Smith (1990) Science 249, 386–390; Devlin (1990) Science 249, 404–406; Cwirla et al. (1990) PNAS USA 87, 6378–6382; Felici (1991) J Mol Biol 222, 301–310; and U.S. Pat. No. 5,223,409).

To identify compounds that decrease the RRM2 genomic DNA level, modulate expression of a marker nucleotide sequence under the control of a promoter sequence of SEQ ID NO:1, 2, or 3, decrease the level of RRM1 or p53R2 mRNA or protein, decrease the level of RRM1 and RRM2 interaction, or decrease the level of RRM1 and p53R2 interaction in a system, the system is contacted with a candidate compound and the RRM2 genomic DNA level, the expression of the marker nucleotide sequence, the level of RRM1 or p53R2 mRNA or protein, the level of RRM1 and RRM2 interaction, or the level of RRM1 and p53R2 interaction is evaluated relative to that in the absence of the candidate compound. In a cell system, the cell can be one that contains amplified RRM2 genomic DNA (e.g., a cancer cell), one naturally expresses RRM1, RRM2, or p53R2, or one that is modified to express a recombinant nucleic acid, for example, having the RRM1, RRM2, or p53R2 gene fused to a heterologous promoter. When the expression of the marker nucleotide sequence is monitored, the system can contain a transcriptional factor that interacts with the promoter sequence of SEQ ID NO:2, 3, or 4, e.g., SP1, c-Ets, MZF1, E2F, Lyf-1, GATA-X, HSF2, AP-1, CdxA, IK-2, Sox-5, SRY, Brn-2, HNF-1, STATx, GATA-1, USF, Pbx-1, Oct-1, GATA-2, CRE-Bp, or Nkx-2, or a nucleic acid encoding such a transcriptional factor. If the level of RRM2 genomic DNA, RRM1 and RRM2 interaction, or RRM1 and p53R2 interaction is lower in the presence of the candidate compound than that in the absence of the candidate compound, or if the expression of the marker nucleotide sequence in the presence of the candidate compound differs from that in the absence of the candidate compound, the candidate compound is identified as being useful for preventing and treating a cell proliferation-associated disorder.

The RRM2 genomic DNA level can be determined by methods described above and any other methods well known in the art.

The expression of the marker nucleotide sequence, RRM1, or p53R2 can be determined at either the mRNA level or at the protein level. Methods of measuring mRNA levels in a tissue or a body fluid sample are known in the art. In order to measure mRNA levels, cells can be lysed and the levels of mRNA in the lysates or in RNA purified or semi-purified from the lysates can be determined by any of a variety of methods including, without limitation, hybridization assays using detectably labeled DNA or RNA probes and quantitative or semi-quantitative RT-PCR methodologies using appropriate oligonucleotide primers. Alternatively, quantitative or semi-quantitative in situ hybridization assays can be carried out using, for example, tissue sections or unlysed cell suspensions, and detectably (e.g., fluorescently or enzyme) labeled DNA or RNA probes. Additional methods for quantifying mRNA include RNA protection assay (RPA) and SAGE.

Methods of measuring protein levels in a tissue or body fluid sample are also known in the art. Many such methods employ antibodies (e.g., monoclonal or polyclonal antibodies) that bind specifically to the target protein. In such assays, the antibody itself or a secondary antibody that binds to it can be detectably labeled. Alternatively, the antibody can be conjugated with biotin, and detectably labeled avidin (a polypeptide that binds to biotin) can be used to detect the presence of the biotinylated antibody. Combinations of these approaches (including "multi-layer sandwich" assays) familiar to those in the art can be used to enhance the sensitivity of the methodologies. Some of these protein-measuring assays (e.g., ELISA or Western blot) can be applied to lysates of cells, and others (e.g., immunohistological methods or fluorescence flow cytometry) applied to histological sections or unlysed cell suspensions. Methods of measuring the amount of label will be depend on the nature of the label and are well known in the art. Appropriate labels include, without limitation, radionuclides (e.g., $^{125}$I, $^{131}$I, $^{35}$S, $^{3}$H, or $^{32}$P), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). Other applicable assays include quantitative immunoprecipitation or complement fixation assays.

The level of RRM1 and RRM2 interaction, or the level of RRM1 and p53R2 interaction can be determined by any method known in the art, e.g., by in vitro binding assay or by using a yeast hybrid system. The binding domains of RRM1, RRM2, and p53R2 can be identified, e.g., by mutagenesis, and used in the screening assays.

This invention further provides a method for preventing and treating a cell proliferation-associated disorder. Subjects to be treated can be identified, for example, by determining the RRM2 genomic DNA level in a sample prepared from a subject by methods described above. If the RRM2 genomic DNA level is higher in the sample from the subject than that in a sample from a normal subject, the subject is a candidate for treatment with an effective amount of compound that decreases the RRM2 genomic DNA level, transcription from a promoter sequence of SEQ ID NO:1, 2, or 3, the level of RRM1, RRM2, or p53R2 mRNA or protein, or the level of RRM1 and RRM2 or RRM1 and p53R2 interaction in the subject. The term "treating" is defined as administration of a composition to a subject, who has a cell proliferation-associated disorder, with the purpose to cure, alleviate, relieve, remedy, prevent, or ameliorate the disorder, the symptom of the disorder, the disease state secondary to the disorder, or the predisposition toward the disorder. An "effective amount" is an amount of the composition that is capable of producing a medically desirable result, e.g., as described above, in a treated subject. This method can be performed alone or in conjunction with other drugs or therapy.

In one in vivo approach, a therapeutic composition (e.g., a composition containing a compound identified as described above) is administered to the subject. Generally, the compound will be suspended in a pharmaceutically-acceptable carrier (e.g., physiological saline) and administered orally or by intravenous infusion, or injected or implanted subcutaneously, intramuscularly, intrathecally, intraperitoneally, intrarectally, intravaginally intranasally, intragastrically, intratracheally, or intrapulmonarily. For prevention and treatment of cancer, the compound can be delivered directly to the cancer tissue.

The dosage required depends on the choice of the route of administration; the nature of the formulation; the nature of the subject's illness; the subject's size, weight, surface area, age, and sex; other drugs being administered; and the judgment of the attending physician. Suitable dosages are in the range of 0.01–100.0 mg/kg. Wide variations in the needed dosage are to be expected in view of the variety of compounds available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery, particularly for oral delivery.

Alternatively, a polynucleotide containing a nucleic acid sequence encoding an anti-sense RRM1, RRM2, or p53R2 RNA can be delivered to the subject, for example, by the use of polymeric, biodegradable microparticle or microcapsule delivery devices known in the art.

Another way to achieve uptake of the nucleic acid is using liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano et al. (1995) J Mol Med 73, 479). Alternatively, tissue specific targeting can be achieved by the use of tissue-specific transcriptional regulatory elements (TRE) which are known in the art. Delivery of "naked DNA" (i.e., without a delivery vehicle) to an intramuscular, intradermal, or subcutaneous site is another means to achieve in vivo expression.

In the relevant polynucleotides (e.g., expression vectors), the nucleic acid sequence encoding an anti-sense RRM1, RRM2, or p53R2 RNA is operatively linked to a promoter or enhancer-promoter combination. Enhancers provide expression specificity in terms of time, location, and level. Unlike a promoter, an enhancer can function when located at variable distances from the transcription initiation site, provided a promoter is present. An enhancer can also be located downstream of the transcription initiation site.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles that are suitable for administration to an animal or a human, e.g., physiological saline or liposomes. A preferred dosage for administration of polynucleotide is from approximately $10^6$ to $10^{12}$ copies of the polynucleotide molecule. This dose can be repeatedly administered, as needed. Routes of administration can be any of those listed above.

Antibodies (monoclonal or polyclonal) to RRM1, RRM2, or p53R2 can be used to reduce the level of RRM1, RRM2, or p53R2 protein, or to decrease the level of RRM1 and RRM2 or RRM1 and p53R2 interaction in a subject. The term "antibody" includes intact molecules as well as fragments thereof, such as Fab, F(ab')$_2$, and Fv which are capable of binding to an epitopic determinant present in the RRM1, RRM2, or p53R2 protein. Methods of making monoclonal and polyclonal antibodies and fragments thereof are known in the art. See, for example, Harlow and Lane, (1988) Antibodies: A Laboratory Manual, Cold Spring Harbor Laboratory, New York.

Other compounds that can be used to inhibit RRM1 and RRM2 or RRM1 and p53R2 interaction include a peptide or polypeptide containing an amino acid sequence at the C-terminus of RRM2. For example, a 7-amino acid peptide (FTLDADF, SEQ ID NO:5) at the C-terminus of RRM2 was found to dramatically suppress the human RR activity when added to the enzyme in vitro at a ratio of 10:1 (peptide: enzyme). It was further observed that a truncated form of the M2 subunit, lacking these 7 amino acids at the C-terminus, fails to form a complex with the corresponding large subunit M1. These results suggest that the 7-amino acid peptide may compete with M2 for a binding site on M1. Unexpectedly, the inhibition of the RR activity by this peptide is superior than that caused by currently used RR inhibitors such as hydroxyurea and triapine. Further studies revealed that a portion of the 7-amino acid peptide (e.g., a 5-mer or a 3-mer) can also inhibit the RR activity. Thus, methods of treating a cell proliferation-associated disorder using the peptide of SEQ ID NO:5 or its functional equivalents are within the scope of the invention. Peptides or polypeptides that are functionally equivalent to SEQ ID NO:5 can be either longer or shorter than SEQ ID NO:5, or contain substitute amino acids within SEQ ID NO:5, as long as they are capable of inhibiting the interaction between RRM1 and RRM2 or RRM1 and p53R2. Such peptides or polypeptides can be generated and used according to the methods described above or any other methods well known in the art.

In addition, the invention provides a method of developing a procedure for treating a cell proliferation-associated disorder by providing a plurality of subjects suffering from a cell proliferation-associated disorder (e.g., subjects having amplified RRM2 genomic DNA); administering to each subject an effective amount of an RRM2 inhibitor (e.g., hydroxyurea) followed by an effective amount of a nucleotide or nucleoside analog (e.g., gemcitabine), each at a unique time point; and selecting an optimal time point at which the cell proliferation-associated disorder is inhibited to the greatest extent. Once the optimal time point has been identified, the procedure can be used to treat a cell proliferation-associated disorder in appropriate subjects.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

EXAMPLE I

Characterization of the Human Ribonucleotide Reductase M2 Subunit Gene; Genomic Structure and Promoter Analyses Materials and Methods (1) Cloning and Sequencing of Human RRM2 Genomic DNA A human placental genomic library (Human Genome Systems) was screened using a pair of primers specific for the hRRM2 structural gene:
hRRM204: 5' ATTTAGAAGTCAGCATCCAAG 3', and
hRRM208: 5' TACACAAACCATCGGAGGAGAGAG 3'.

After three positive clones (clone 13999, 14000, and 14001) were selected, the Sac I restriction enzyme was employed to digest DNA isolated from the selected clones. Southern blot analysis was then preformed. Bands of 6.2 and 5.1 kb were identified and subcloned into the PCNTR vector (5'®3' Genome Systems). These clones were designated as P6.2 and P5.1 respectively. Sequencing was performed on both clones to generate the genomic sequence map of the full-length hRRM2 genomic DNA.

(2) Identification of Transcription Initiation Sites by 5'RACE

Total RNA was isolated from human KB cells according to the standard protocol. The cDNA clones representing the 5'-termini of RRM2 mRNA were obtained by 5'RACE following the manufacturer's protocol (BRL Lifesciences). The primers used to identify the transcription initiation sites corresponded to the hRRM2 cDNA sequence (GenBank Accessing Number x59618) (Pavloff et al. (1992) DNA Seq 2 (4), 227–234) at positions 358 to 338 (hRRM225: 5' GGCTCCTGGAAGATCCTCCT 3') and at positions 242 to 225 (hRRM231: 5' CTGCTGCGGGTCCGTGAT 3').

(3) Generation of RRM2 Promoter and Reporter Construct

A luciferase reporter plasmid containing the 5'-flanking region of the hRRM2 gene from bp 1787 to bp 2581 of SEQ ID NO:1 was constructed by inserting a designated DNA fragment from P6.2 subclone into the pGL3-basic vector (Promega) using the Erase A Base technique.

(4) Cell Culture and Transient Transfections

Human oropharyngeal carcinoma KB cells (American Type Culture Collection) were cultured on plastic tissue culture plates in RPMI 1640 medium supplemented with 10% fetal calf serum and 100 units/ml of penicillin and streptomycin at 37° C. in a humidified atmosphere containing 5% carbon dioxide. PC-3 human prostate cancer cells (American Type Culture Collection) were grown under the same conditions. Transient transfections were performed using lipofectin according to the manufacturer's suggested protocol (BRL Lifesciences). Briefly, cells were cultured in 60 mm cell culture dish at a density of $1 \times 10^5$ cells/dish and transfected with 5 mg/dish of the reporter plasmid.

(5) Measurement of Promoter Activity

Cells were transfected with reporter plasmids expressing luciferase from the inserted promoter fragments. Two days after transfection, cells were lysed and luciferase activity was measured in a luminometer using a luciferase assay kit (Promega). Luciferase activity was standardized by adjusted protein concentration (BioRad). Control transfections were performed using the pGL3-basic parent plasmid with no promoter insert, the PGL3 promoter plasmid containing the SV40 promoter, and the pGL3 control plasmid containing the SV40 promoter and enhancer region. Experiments were performed in duplicates for at least three times.

(6) Northern Blot Analysis of hRRM2 mRNA Expression in Various Human Tissues

Premade nylon filters bound with approximately 2 mg/lane of polyA mRNA from various human tissues (heart, brain, placenta, lung, liver, skeletal muscle, kidney, and pancreas) were obtained from Clontech Laboratories (Palo Alto, Calif.). Filters were probed with full-length hRRM2 cDNA under stringent conditions using quick hybridization buffer (Stratagene) (Yen et al. (1994) Cancer Res 54, 3686–3691).

(7) hRRM2 Expression After Treatment of Chemotherapeutic Agents and UV Irradiation PC-3 prostate cancer cells were treated with $IC_{50}$ dose of each chemotherapeutic agent for 48 hours before RNA was extracted from the cells. In order to induce DNA damage, KB cells were exposed to 2000 J/min UV irradiation and then returned to normal culture conditions. RNA was then extracted at various times. Gel electrophoresis was performed and 20 mg of total RNA was loaded in each lane. The separated RNA was transferred to a membrane and probed with full-length hRRM2 cDNA as described above. Blots were also probed with GAPDH housekeeping gene as an internal control for RNA loading. Blots were quantified on PhosphorImager. The intensities of the bands in each lane were normalized to the intensity of the GAPDH band.

Results (1) Cloning and Sequencing of Genomic hRRM2

In previous studies, the RRM2 gene was localized to chromosome 2 (2p24-p25). In addition, 3 pseudogenes were found on other chromosomes (1p31-p33, 1q21-q23, and Xp11-p21) (Yang-Feng et al. (1987) Genomics 1, 77–86). Using a probe specific for the RRM2 structural gene, a human placental genomic library was screened and three PAC clones containing portions of the desired gene were identified. These fragments were subcloned into the PCNTR vector and sequenced in their entirety. The gene was found to consist of 10 exons. The intron/exon junctions, shown in Table 1, correspond to consensus splicing signals.

site corresponding to the 1.65 kb mRNA is designated as +1 (corresponding to bp 2567 of SEQ ID NO:1) while transcription of the 3.4 kb mRNA was found to initiate at position −187 (corresponding to bp 2380 of SEQ ID NO:1). The site that has been designated as +1 here corresponds to +151 in the RRM2 sequence published by Pavloff et al. ((1992) DNA Seq 2 (4), 227–234). A consensus TATA box was found upstream of the first transcription initiation site by manual scanning, but no such site was found upstream of the second transcription initiation site. Further analysis of the promoter region was performed using the TFSEARCH data base in conjunction with the TRANSFAC MATRIX TABLE for transcription factor prediction. Potential DNA binding sites for several transcription factors were identified. Three consensus CCAAT boxes were found in the region between the two transcription start sites at positions −82, −109, and −139 and one additional site was found to lie further upstream at position −436. The CCAAT boxes in the promoter proximal region have been implicated in the activation of hRRM2 expression (Park and Levine (2000) Biochem and Biophys Res Comm 267, 651–657). SP1 binding sites are also known to play a role in determining the

TABLE 1

Exon/intron Junction of Human RR M2 Gene

| Exon Number | Intron | Exon | Exon Size (bp) | Exon | Intron | Intron Size (kp) |
|---|---|---|---|---|---|---|
| 1 | gctgcgcttg SEQ ID NO:22 | AAAATCGCGC SEQ ID NO:32 | 330 | GGAGAACACG SEQ ID NO:42 | gtgagccctc SEQ ID NO:51 | 0.085 |
| 2 | ctccccgcag SEQ ID NO:23 | CCGCCGGCCC SEQ ID NO:33 | 75 | CACGGAGCCG SEQ ID NO:43 | gtgagtggcg SEQ ID NO:52 | 0.329 |
| 3 | cccccaacag SEQ ID NO:24 | AAAACTAAAG SEQ ID NO:34 | 146 | CCGAGGAGGT SEQ ID NO:44 | aatcggagga SEQ ID NO:53 | 0.204 |
| 4 | gaacctcagg SEQ ID NO:25 | TGACCTCTCC SEQ ID NO:35 | 115 | TGAAAACTTG SEQ ID NO:45 | gtgagtttcc SEQ ID NO:54 | 0.863 |
| 5 | ttgccactag SEQ ID NO:26 | GTGGAGCGAT SEQ ID NO:36 | 134 | CCAAAGAAAG SEQ ID NO:46 | gtgagtattc SEQ ID NO:55 | 2.01 |
| 6 | tgcctactag SEQ ID NO:27 | GGAATTTCTC SEQ ID NO:37 | 95 | GCTACCTATG SEQ ID NO:47 | gtaaggagac SEQ ID NO:56 | 0.118 |
| 7 | tcctaaatag SEQ ID NO:28 | GTGAACGTGT SEQ ID NO:38 | 134 | CAGAGATGAG SEQ ID NO:48 | gtgagtgtaa SEQ ID NO:57 | 1.635 |
| 8 | tttttctag SEQ ID NO:29 | GGTTTACACT SEQ ID NO:39 | 105 | GATAGAACAG SEQ ID NO:49 | gtaaagtggg SEQ ID NO:58 | 0.088 |
| 9 | tggttcctag SEQ ID NO:30 | GAGTTCCTCA SEQ ID NO:40 | 114 | TTTTAGCAAG SEQ ID NO:50 | gtaaagtatt SEQ ID NO:59 | 0.08 |
| 10 | ccctttcag SEQ ID NO:31 | GTTTTCAGAG SEQ ID NO:41 | 1263 | | | |

Two hRRM2 cDNAs of 3.4 kb and 1.65 kb have been identified. They include identical coding regions and differ only in the lengths of their untranslated regions. These cDNAs are shown to be aligned with the genomic structure. The human RRM2 gene was found to show significant structural similarity to the mouse RRM2 gene, which also consists of 10 exons.

(2) Identification of Transcription Initiation Sites by 5'-RACE

In order to identify the promoter region and transcription start sites for the two mRNA transcripts, primer extension and 5'-RACE were employed. The transcription initiation site of transcription initiation. Putative SP1 binding sites have been identified at −480 and several additional positions further upstream. Other putative transcription factor binding sites include c-Ets, MZF1, E2F, Lyf-1, GATA-X, HSF2, AP-1, CdxA, IK-2, Sox-5, SRY, Brn-2, HNF-1, STATx, GATA-1, USF (c-Myc), Pbx-1, Oct-1, GATA-2, CRE-Bp, and Nkx-2 sites.

(3) Characterization of the hRRM2 Promoter

In order to further characterize the hRRM2 promoter, several deletion constructs were generated to drive transcription of a luciferase gene. These constructs extend through position +1 and have end points at positions −659, −557, −455, −257, −236, −204, −184, −156, −106, and −55. As transcription initiation sites were found at both position +1 and position −187, the 6 longest promoter deletion constructs have the potential to initiate transcription from both sites while the 4 shortest promoter constructs retain only the downstream initiation site. Relative luciferase activity for these reporter constructs after transfection into KB cells was determined. A deletion to −659 was found to express luciferase at a level comparable to the pGL3 promoter control in which luciferase expression is driven by the SV40 promoter lacking any enhancer sequence. Luciferase activity dropped only minimally for deletions between −659 and −257, and then a significant drop in activity occurred with deletion of the sequence between −257 and −236. As there are no identified binding sites for transcription factors within this region, it is unlikely that this change in activity reflects a change due to such a factor. The proximity of the upstream site of transcription initiation suggests that the drop in activity may reflect the presence of two separate RRM2 promoter regions, wherein the region between −659 and −257 acts as a promoter for the 3.4 kb RRM2 mRNA while the region between −204 and +1 acts as a promoter for the 1.65 kb RRM2 mRNA. This is supported by the observation that significant promoter activity is again observed for the deletion constructs with endpoints at −204, −184, and −156. Luciferase activity again dropped significantly with the deletion of the sequence between −156 and −106, suggesting that some important site was lost. There are two CCAAT boxes within this segment of DNA which are likely to be responsible for this drop in activity.

(4) Differential Expression of hRRM2 mRNA Transcripts in Human Tissues

As two hRRM2 transcripts have been identified and they appear to be expressed from separate promoters, whether they lead to different expression patterns was further examined. In order to determine whether they are differentially expressed in a tissue specific manner, Northern blot analysis was used to measure the level of each transcript in a variety of human tissues. All tissues examined expressed both forms of mRNA, although their relative levels varied significantly. In placenta, lung, and kidney, the 3.4 kb mRNA is the major form. Conversely, in thymus, testis, colon, and small intestine, the 1.65 kb form predominates. The gene is expressed at high levels in thymus, small intestine, colon, and testis, and at lower levels in lung and liver. Very low levels were detected in prostate, skeletal muscle, brain and leukocyte tissues. Interestingly, the size of the hRRM2 mRNA found in the heart tissue was slightly larger than the others, which may reflect differential splicing or alternative transcription.

(5) Alteration of hRRM2 mRNA Expression Induced by Chemotherapeutic Agents or UV Treatment The presence of two promoters driving transcription of hRRM2 may also reflect a need to have multiple means of regulating expression in response to different cellular events. In particular, hRRM2 may require one set of regulatory factors to control expression levels throughout cell cycle and a different means for regulating expression in response to DNA damage. In order to address this possibility, the effect of various chemotherapeutic drugs and of UV irradiation on the relative expression levels of the two forms of hRRM2 mRNA was examined. PC-3 prostate cancer cell was treated with the $IC_{50}$ dose of each agent for 48 hours, and RNA was extracted and examined by Northern blot. The expression of each form of hRRM2 mRNA in drug-treated cells was measured as a relative ratio to the level in untreated cells. Treatment with interferon led to a slight up-regulation of both mRNAs, whereas the cell treated with fludarabine, a nucleotide analog revealed no regulation on neither mRNAs. Cells treated with CPT-11, a topoisomerase I inhibitor, showed a significant down-regulation of both forms of mRNA but 1.65 kb mRNA predominately. Treatment with taxol, a microtublin inhibitor, showed down-regulatory effect on the level of both mRNA relative to the untreated cells. While the expression of hRRM2 clearly was affected by some of these drugs, the effect was not specific to one form of the mRNA. Instead, the changes in expression levels were reflected in both transcripts.

In order to more specifically examine the effect of DNA damage on the level of hRRM2 expression, cells were exposed to UV irradiation, and then RNA was extracted from cells after 6, 24, and 48 hours. The amount of each hRRM2 mRNA after UV treatment is measured relative to the level in untreated cells. Again, both forms of hRRM2 mRNA are affected in a similar manner by UV treatment. Expression is significantly increased after 6 hours, after which the level dropped back to the level found in untreated cells by 24 hours, and then significantly reduced at the 48-hour time point. The level of induction after 6 hours suggests that the downstream promoter may be preferentially regulated.

EXAMPLE II

Human Ribonucleotide Reductase M2 Subunit Gene Amplification and Transcriptional Regulation in a Homogeneous Staining Chromosome Region Responsible for the Mechanism of Drug Resistance Materials and Methods (1) Cells Human oropharyngeal carcinoma KB cells (American Tissue Culture Collection, Manassas, Va.) were grown in plastic tissue culture plates in RPMI 1640 supplemented with 10% fetal bovine serum at 5% $CO_2$ at 37° C. A gemcitabine-resistant clone (KBGem) was selected by stepwise exposure to increasing concentrations of gemcitabine. This cloned cell line was selected and maintained in the presence of 8 mM gemcitabine. The $ID_{50}$ of KB wild-type (KBwt) cells is 0.3 mm, whereas the KBGem clone possesses an $ID_{50}$ of 32.3 mm (Goan et al. (1999) Cancer Res 59, 4204–4207). A hydroxyurea-resistant clone (KBHURs) was sequentially selected in a stepwise manner in the presence of HU. This cloned cell line was selected in the presence of 1 mM HU (Yen et al. (1994) Cancer Res 54, 3686–3691). To avoid contamination, these two clones were selected and maintained separately by different personnel and facilities.

(2) Probes, Primers, and PCR

The genomic sequence of the human M2 subunit of RR has been published (GenBank Accession Number AY032750) (Zhou et al. (2001) Cytogent Cell Genet 95, 52–59). The following PCR primers were designed to amplify the promoter region of hRRM2 based on the published genomic sequence:

```
PAC 621:    5'GATCGCTTGATACCAACCTGGG 3',

PAC 624:    5'GGCCACGCCGACATGACTCA 3',

PAC 6210:   5'TCCCTGGGAGATGGATGC 3',
```

-continued

PAC 6211:   5'AAGCCTGGAAAACGCTCC 3',

PAC 6228:   5'TCCCGTAGTTTGAAGGTTTACAA 3', and

HRM 228:    5'ACTCCAGCAGCCTTTAAATCTC 3'.

A hot start PCR technique was employed (Qiagen, Calif.). The reaction was initiated by heating for 15 min at 95° C., followed by 35 cycles of 40 sec at 94° C., 40 sec at 55° C. and 2 min at 72° C., followed by a final incubation for 7 min at 72° C.

(3) RRM2 mRNA and Northern Blot Analyses

Total RNA was extracted from logarithmically growing cells, or from cells growing under specified conditions as described previously (Goan et al. (1999) Cancer Res 59, 4204–4207). The RNA was resolved in a formaldehyde-agarose gel and blotted onto a Hybond-N membrane (American, Arlington, Ill.). Radioactive probes for detecting hRRM2 were prepared as described previously (Goan et al. (1999) Cancer Res 59, 4204–4207). GAPDH was used as an internal control. Hybridizations were performed under stringent conditions. RNA was cross-linked to membranes by UV light for 1 min. A random priming probe kit from Roche (Indianapolis, Ind.) was used to label the probes. The blots were hybridized for 1 hr at 68° C. with $^{32}$P-labeled probes. After washing twice with 2×SSC/0.1% SDS and twice with 0.1×SSC/0.1% SDS, membranes were exposed for 18–48 hr at −70° C. to Kodak XAR-5 film (Eastman Kodak, Rochester, N.Y.) with intensifying screens or exposed to a PhosphoImager screen for 18 hr and then scanned by a PhosphoImager.

(4) RRM2 Protein and Western Blot Analyses

Protein extracts from each clone were separated by 10% SDS-PAGE, loaded with equal amounts of proteins. Following electrophoresis, the proteins were transferred to a PVDF membrane (American Pharmacia Biotech). Goat anti-human RRM2 polyclonal antibody, purchased from Santa Cruz Biotechnology, Inc. (SC-10844:R2(N-18)), was used for Western blot analysis. The α-tubulin anti-serum was employed as an internal control.

(5) Gel Shift Assay a. Nuclear Protein Extraction

1×10$^7$ cells were washed with cold PBS and suspended in 400 ml Buffer A (10 mM HEPES, pH 7.9, 10 mM KCl, 0.1 mM EDTA, 0.1 mM EGTA, 1 mM DTT and 0.5 mM PMSF) for 15 minutes. After adding 25 ml Nonidet P40, the cell pellets were transferred into 1.5 ml Eppendorf tubes, mixed by vortexing for 10 seconds, centrifuged at 8,000–10,000 rpm and 4° C. for 30 seconds. The pellets were resuspended in 50 ml Buffer B (20 mM HEPES, pH 7.9, 0.4 M NaCl, 1 mM EDTA, 1 mM EGTA, 1 mM DTT and 1 mM PMSF) and vigorously rocked at 4° C. for 15 minutes. The extracts were then centrifuged (10,000 rpm at 4° C.) for 15 minutes, and the supernatant was collected (approximately 55 ml) and stored at −80° C.

b. DNA Sequences of in vitro Synthesized Double-Stranded DNA Fragments

DNA sequences of in vitro synthesized double-stranded DNA fragments are as follows:

SP1:         5'ATTCGATCGGGGCGGGGCGAGC 3'

AP-1 (c-jun): 5'CGCTTGATGAGTCAGCCGGAA 3'

-continued

AP-2:    5'GATCGAACTGACCGCCCGCGGCCCGT 3'

NF-κB:   5'AGTTGAGGGGACTTTCCCAGG 3'

OCT1:    5'TGTCGAATGCAAATCACTAGAA 3', and

CREB:    5'AGAGATTGCCTGACGTCAGAGAGCTAG 3'.

c. End-labeling of Consensus Oligonucleotides

The in vitro synthesized double-stranded DNA fragments were labeled with γ-$^{32}$P ATP using T4 polynucleotide kinase according to the standard protocols. Unincorporated nucleotides were removed using Micro-Bio-spin P-30 spin columns (Bio-Red).

d. DNA-Protein Binding and Gel Shift

DNA-protein binding reactions were performed in Binding Buffer consisting of 4% glycerol, 1 mM MgCl$_2$, 0.5 mM EDTA, 0.5 mM DTT, 50 mM NaCl, 10 mM Tris-HCl (pH 7.5) and 0.05 mg/ml poly (dI-dC). Nuclear lysates were pre-incubated for 10 minutes at room temperature. End-labeled probes were then added and incubated for an additional 20 minutes at room temperature. DNA-protein complexes were separated on a 6% DNA retardation gel (Invitrogen) in 0.5×TBE at 250 volts for 1 hour. Dried gels were analyzed on PhosphoImager.

(6) Spectral Karyotyping Analyses

To identify the marker chromosome, 24-color spectral karyotyping (SKY) was performed. Slides were prepared using recently harvested material (test samples) or residual cell pellets (validation samples) and stored at room temperature overnight. Metaphase cells, devoid of cytoplasm, and slide preparation dropped within 24 hr of analysis, without artificial aging, provided the best spectral karyotyping results. Before hybridization, slides were treated with 0.1 mg/ml RNase A in 2×SSC, pH 7.0, 37° C. for 45 min, digested with pepsin (Sigma, St. Louis, Mo.) (6 mg/ml in 0.01 N HCl, 37° C.) for 1 min, and fixed in formaldehyde (1% in 1×PBS/50 mM MgCl$_2$, room temperature) for 10 min. Slides were denatured in 70% formamide/2×SSC, pH 7.0, at 72° C. for 2 min. SKY paints were denatured at 72° C. for 5 min and preannealed at 37° C. for 1 hr. Denatured probes were applied to the denatured slides and incubated at 37° C. for 48 hr. Post-hybridization washes were performed per probe manufacturer's instruction. Nuclei and metaphase chromosomes were counterstained with DAPI. Metaphase images were captured and analyzed on a SKY vision cytogenetic workstation (Applied Spectral Imaging) attached to a Zeiss Axioplan 2 microscope with a 150 W Xenon UV light source. Five fluorochromes were used in the SKY combinatorial labeling: Spectrum Orange, Texas Red, Cy5, Spectrum Green, and Cy5.5. Instrument adjustments were implemented to reduce artifact caused by weak fluorescence signals or misalignment of the optical system prior to initiation of the study (Garini et al. (1999) Cytometry 35, 214–226). For each clone, 20 or more GTG-banded metaphase cells were analyzed. For spectral karyotyping validation, 5 to 20 metaphase cells were analyzed.

(7) FISH Analyses

Standard FISH analyses were performed to verify discrepant results. The following probes were used: chromosome enumeration satellite DNA probes (Vysis, Downers Grove, Ill.) for chromosomes 16, 17, and 20; whole chromosome painting probes (Oncor, Gaithersburg, Md.) for chromosomes 3, 6, 7, 9, and 11; region-specific probes including YAC (YA153A6) for BCL2 (provided by Dr. Gary A. Silverman, Harvard Medical School, Boston, Mass.), YAC (812f11) for AML1 (provided by Dr. Katherine Gardiner, Eleanor Roosevelt Cancer Center, Buffalo, N.Y.), chromosome arm 12p and 12q arm-specific paint probes (AL Technologies, Rockville, Md.), chromosome arm 19q telomere probe (Vysis), translocation probe (Oncor), chromosome 22 BCR probe (Oncor), and MYCN locus-specific probe (Oncor). All FISH procedures using commercially available probes followed the manufacturers' protocols. Formamide post-hybridization washes were used for YAC-based FISH analyses (Applied Spectral Image, Ill.).

(8) Synchronization Study

KBwt and KBGem and KBHURs clones were synchronized by growing the cells in starvation conditions (0.25% serum for 96 hrs) and then returning to normal growth conditions (with 10% FBS). At the designated time points after returning to serum-containing medium, $0.5–1\times10^8$ cells were harvested and total RNA was extracted for Northern blot analysis as described above.

Results (1) Detection of Amplified hRRM2 Sequences on the Homogeneous Staining Chromosome Region The KBwt cell line was found to be near triploid (~3n) with hRRM2 hybridization signals on the short arm of three "A group" chromosomes. DAPI staining identified the "A group" chromosomes as human chromosome 2. The spectrum green labeled hRRM2 PAC DNA probe exhibited signals on chromosome 2p 24-25 of mitotic cells. The gene copy number of hRRM2 genes was correct for the 3n ploidy level of these cells. Amplified hRRM2 gene sequences were not observed in KBwt cells. An isochromosome for the short arm of chromosome 2 was not observed in either metaphase cells (n=10) or interphase nuclei (n=50).

Partial G-banding analysis of the KBGem clone exhibited a modal range of near triploid. Hybridization signals were localized to two morphologically normal chromosome 2s, an isochromosome of the short arm of chromosome 2 or i(2)(p10), and a highly amplified region on a marker chromosome. To identify the marker chromosome, 24-color spectral karyotyping (SKY) was performed. SKY painting indicated the marker chromosome was a derivative of chromosome 13. Using ISCN, 1995 nomenclature, the hsr-bearing derivative chromosome 13 may be described as der(13)del(13)(q12q14)t(2;13)(p24;p11.2)hsr(2)(p24p25). Furthermore, partial G-banding analysis of the KBHURs clone exhibited near triploidy with a highly amplified marker chromosome apparently derived from an I(2p). SKY painting indicated that the marker chromosome also contained chromosome 5 material. FISH using a chromosome 5 painting probe confirmed the chromosome 5 material at the distal end of the der (2) marker chromosome. Suggested nomenclature for this marker is: der(2) i(2) (p10) inv dup hsr (2) (p24 p25)t (2;5) (p25; ?).

(2) Gene Amplification of hRRM2 is Correlated with hsr Amplification

In an attempt to confirm the results from the cytogenetic experiments showing the hsr amplification, PCR was performed to detect amplification of the hRRM2 promoter region. Significantly higher amplification of hRRM2 was demonstrated for the KBGem clone and KBHURs clone. This result suggests that hRRM2 gene amplification, including the promoter region, may lead to a higher transcription level in KBGem and KBHURs clones relative to KBwt cells. PCR products from each cell line were sequenced and no mutations were found in the amplified region of DNA.

(3) hRRM2 mRNA and Protein Expression in the KBGem and KBHURs Clones

In order to determine whether the observed amplification of the hRRM2 gene led to increased gene expression, total RNA was extracted from each cell line and analyzed via Northern blot to measure the level of hRRM2 mRNA expression. The two forms of hRRM2 mRNA (3.4 kb and 1.65 kb) were detected by the M2 probe. There was significantly higher expression of hRRM2 mRNA in the KBGem and KBHURs clones compared to the KBwt cell line. This observation was consistent with previously published results (Goan et al. (1999) Cancer Res 59, 4204–4207). The KBGem and KBHURs clones expressed the 1.65 kb form of hRRM2 mRNA at a level 30-fold higher than that of KBwt. The 3.4 kb form of hRRM2 mRNA expression in the KBGem clone and the KBHURs clone increased 25-fold relative to KBwt. The 1.65 kb mRNA corresponds to transcription from the downstream P1 promoter and the 3.4 kb mRNA corresponds to expression initiated from the upstream P2 promoter (Zhou et al. (2001) Cytogenet Cell Genet 95, 52–59). To determine the amount of hRRM2 protein, equal amounts of total protein extracted from KBwt, KBGem and KBHURs were analyzed by Western blot. The molecular weight of M2 protein is 44 kD. After quantitation, normalized to a-tubulin, KBGem showed a 10.2-fold and KBHURs showed an 11.3-fold increase over KBwt.

(4) Transcription of hRRM2 Gene in Synchronization Experiments

To better understand hRRM2 mRNA metabolism, the transcription rate of hRRM2 mRNA was further examined in serum-synchronized KBwt, KBGem and KBHURs clones. Total RNA was isolated from cells synchronized by serum starvation for 96 hours in 0.25% FBS. The cells were then returned to normal growth conditions with 10% FBS. Total RNA was examined for each cell line at designated time points between 4 h and 12 h after return to normal growth conditions. While there was little induction of expression in the KBwt cells, the rate of hRRM2 transcription in the KBGem and KBHURs clones increased significantly by 4 hours and continued to increase through 8 and 12 hours. Compared to KBwt cells, the KBGem and KBHURs clones expressed 5 times more hRRM2 mRNA at the 4-hour time point. After 8 hours, the resistant clones exhibited 10-fold higher expression than the wild-type control. At the 12-hour time point, the KBGem and KBHURs clones expressed hRRM2 at a level 20–25-fold higher than that of KBwt. In these clones, the 3.4 kb mRNA expression was equal to that of the 1.65 kb mRNA at the 4- and 8-hr points, but at 12-hr point, the 1.65 kb mRNA was significantly overexpressed in both resistant clones. As previously reported for the KBHURs clone, overexpression of hRRM2 mRNA and protein led to a 15-fold increase in resistance to HU over KBwt cells (Yen et al. (1994) Cancer Res 54, 3686–3691; and Zhou et al. (1995) Cancer Res 51, 1328–1333). The mechanism of resistance for the KBGem clone was shown to result from an increase in the dCTP pool size (Goan et al. (1999) Cancer Res. 59, 4204–4207). In this clone, overexpression of hRRM2 and the subsequent increase in RR activity leads to an increase in the concentration of dCTP in cells. As a result, the available dCTP is able to compete with dFdCTP, the active form of Gem, leading to a 10-fold increase in resistance.

(5) Transcription Factor Binding to the Amplified hRRM2 Promoter Region

While amplification alone would be expected to lead to increased transcription, changes in transcription factor availability and binding may additionally alter the regulation of hRRM2 expression in these clones. In order to determine whether amplification of the hRRM2 gene led to altered transcription regulation in the drug resistant clones, the binding of transcription factors to identified sites within the hRRM2 promoter was examined. The binding of transcription factors present in KBwt, KBGem and KBHURs nuclear extracts to transcription factor consensus oligonucleotides was studied. Gel shift assays were performed using oligonucleotides of consensus binding sequences for AP-1, Sp1, AP-2, CREB, NF-κB and OCT1 (Briggs et al. (1986) Science 234, 47; Lee et al. (1987) Cell 49, 741; and Lenardo et al. (1989) Cell 58, 227), which were selected based on the analysis of the hRRM2 genomic sequence (Zhou et al. (2001) Cytogenet and Cell Genet 95, 52–59). The interaction of these transcription factors in KBwt, KBGem and KBHURs nuclear extracts demonstrated different DNA-protein binding patterns. The KBGem clone showed a unique binding pattern for Sp1 where an additional band is readily apparent when comparing KBGem sample to KBwt sample. Furthermore, this additional band was competed out by unlabeled Sp1 oligonucleotide, suggesting that the binding was specific. Additional binding was also demonstrated for NF-κB. The KBGem sample shows an additional band on the NF-κB gel that was competed out. The KBGem clone did not demonstrate a different binding pattern for AP-1, AP-2, CREB, and OCT1 when compared to KBwt. However, with AP-1, KBGem clone showed less binding than KBwt. In contrast, the binding of AP-2, CREB, and OCT1 was more prominent for the KBGem clone than KBwt. For the KBHURs clone, different DNA-protein complexes were seen for almost all of the transcription factors examined when compared to KBwt or KBGem. In each case, a slower migrating band than that seen for KBwt and KBGem formed. The slow moving band could be identified on all of the gels. This result supports the premise that KBHURs is regulated by different transcription factors than KBwt that may form a larger protein complex when bound to DNA. Competition with unlabeled oligonucleotides further confirmed the specificity of binding for all of the factors except AP-2 and OCT-1. This finding suggests that the KBHURs clone exhibits a unique pattern of specific binding for AP-1, Sp1, CREB and NF-KB. These findings also suggest that while both KBHURs and KBGem overexpress hRRM2 mRNA from the amplified hRRM2 genes, regulation of the expression by transcription factors is altered.

EXAMPLE III

Time and Sequence Dependence of Hydroxyurea in Combination with Gemcitabine in Human KB Cells Materials and Methods (1) Cells Human oropharyngeal carcinoma KB cells (American Type Culture Collection) were cultured on plastic tissue culture plates in RPMI 1640 supplemented with 10% fetal bovine serum at 37° C. in a humidified atmosphere containing 5% carbon dioxide. Growth media were dialyzed to remove purines and pyrimidines in all Gem studies. In all studies, HU was included in the growth medium where indicated at a concentration of 0.1 mM while Gem was provided at a concentration of 0.3 μM.

(2) Templates, Primers, Radioactive Materials

All templates and primers were synthesized at the City of Hope facility. $^3$H-dATP and $^3$H-dTTP were purchased from Moravek Biochemicals. $^3$H-Gem was customer-labeled by Moravek.

(3) Colony-Forming Assay

The colony-forming ability of KB cells treated with HU and/or Gem at varying times was determined. Equal numbers of logarithmically growing cells were treated with HU and/or Gem at the times specified and then plated in 6-well tissue culture dishes as previously described (Zhou et al. (1998) Biochem Pharmaco 55, 1657–1665). The numbers of colonies, consisting of at least 50 cells, for each sample were counted after incubation at 37° C. for 8 generation times.

(4) Measurement of $^3$H-2'-Deoxycytidine and $^3$H-Gem Incorporation into DNA $5 \times 10^5$ cells were seeded in 35-mm dishes and then treated with 0.1 mM HU. At the indicated time points, 7 μl of $^3$H-2'-Deoxycytidine or 4 μl of $^3$H-Gem was added and the plates were incubated for 30 minutes at 37° C. in a humidified atmosphere containing 5% carbon dioxide. The plates were then harvested, the DNA purified, its concentration measured, and 10 μg of DNA were suspended in 5 ml Ecoscint A and counted for radioactivity using a Beckman LS 5000 CE liquid scintillation counter.

(5) Northern Blot Analysis

Total RNA was extracted from logarithmically growing cells as described previously (Yen et al. (1994) Cancer Res 54, 3686–3691). RNA was electrophoresed in a formaldehyde-agarose gel and blotted onto Hybond-N membrane. Hybridization was performed under stringent conditions using radioactive probes that were prepared as described previously (Zhou et al. (1998) Biochem Pharmaco 55, 1657–1665).

(6) Western Blot Analysis.

Protein extracts from each clone, containing equal amounts of protein (100 μg), were separated by 14% SDS-PAGE and then transferred to PVDF membrane (Amersham Pharmacia Biotech). After transferred, the PVDF membranes were suspended in 1% I-block™ (Applied Biosystems) blocking buffer until detection. Goat anti-human RRM2 polyclonal antibody (Santa Cruz Biotechnology, Inc. (SC-10844:R2(N-18)), and α-tubulin anti-serum (internal control) (Santa Cruz Biotechnology, Inc.) were 1:200 diluted with blocking buffer including 1% I-block™ reagent and 0.1% Tween-20 detergent (Applied Biosystems). PVDF membranes were incubated with above-mentioned buffer for 45 minutes at room temperature. After washed with 0.5% I-block™ blocking buffer six times, the PVDF membranes were re-incubated with 1% I-block™ blocking buffer including 1:2000 diluted second antibody conjugated to alkaline phosphatase (bovine anti-goat antibody, Santa Cruz) for 30–60 minutes. After washed with 0.5% I-block™ blocking buffer and assay buffer (200 mM Tris, 10 mM $MgCl_2$), the PVDF membranes were loaded a thin layer of CSPD® Ready-to-Use substrate solution (Applied Biosystem) and incubated for 5 minutes, then exposed to X-ray film for 3 minutes.

(7) In Vivo RR Activity Assay $1 \times 10^6$ cells were plated in duplicate in 60-mm dishes. Cells were treated with 0.1 mM HU and harvested at the indicated time points. To permeabilize the cells, they were washed twice in Solution A (150 mM sucrose, 80 mM KCL, 35 mM HEPES, pH 7.4, 5 mM potassium phosphate, pH 7.4, 5 mM MgCl$_2$, 0.5 mM CaCl$_2$), resuspended in 500 µl of cold Solution A containing 0.25 mg/ml lysolecithin, and incubated for 1 minute at 4° C. To measure the activity of ribonucleoside diphosphate reduction and DNA synthesis, 1×10$^6$ permeabilized cells were incubated at 37° C. for 10 minutes in 300 µl of 50 mM HEPES, pH 7.4, 10 mM MgCl$_2$, 8 mM dithiothreitol, 0.06 mM FeCl$_3$, 7.5 mM potassium phosphate, pH 7.4, 0.75 mM CaCl$_2$, 10 mM phosphoenolpyruvate, 0.2 mM $^3$H-rCDP, 0.2 mM rGDP, 0.2 mM rADP, 0.2 mM dTDP. Following incubation, 150 µl of the suspension mixture was taken out, resulting in two samples, and mixed with 30 µl of 60% perchloric acid/0.1% sodium pyrophosphate. After a 15-minute incubation on ice, 1 ml ddH$_2$O was added to dilute the mixture and then it was centrifuged to precipitate any acid-insoluble material. Pellets were extracted with 0.1 ml 0.2 N NaOH and incubated at 37° C. for 30 minutes. 75 µl aliquots were suspended in 5 ml Ecoscint A and counted for radioactivity using a Beckman LS 5000 CE liquid scintillation counter.

(8) Isolation of dNTPs

After treatment at designated time points with HU and/or Gem, cells were trypsinized, washed with PBS and viable cells were counted by Trypan Blue dye exclusion. Cells were transferred to 1.5 ml Eppendorf tubes and pelleted by brief centrifugation. Cell pellets were mixed with 100 µl 15% trichloroacetic acid and kept on ice for 10 minutes. It was then centrifuged for 5 minutes and the supernatant collected. dNTPs were extracted with two 50 µl aliquots of freon/trioctylamine (55%:45%). After each centrifugation, the supernatant was saved. 5 µl aliquots of each sample were used to check dATP, dCTP, dGTP, and dTTP concentrations. Each measurement was performed in duplicate (Zhou et al. (1998) Biochem Pharmaco 55, 1657–1665).

(9) dNTP Pool Assay

This assay, which measures the amount of DNA synthesis generated by an unknown pool of dNTPs, was conducted according to the method of Sherman and Fyfe as previously described (Zhou et al. (1998) Biochem Pharmaco 55, 1657–1665; and Sherman and Fyfe (1989) Anal Biochem 180, 222–226). The reaction mixture contained 50 mM Tris-HCl (pH 7.5), 10 mM MgCl$_2$, 5 mM DTT, 0.25 µM template/primer, 1.25 µM $^3$H-dATP (for dCTP, dGTP, and dTTP assays) or $^3$H-dTTP (for dATP assay), and 0.2 units of Sequenase (2.0) in a total volume of 50 µl. DNA synthesis was allowed to proceed for twenty minutes at room temperature and then the reaction was stopped and 40 µl of the reaction mixture was spotted onto Whatman DE81 ion exchange paper (2.4 cm diameter). The paper was dried, washed with 5% Na$_2$HPO$_4$ (3×10 min.), and rinsed once with distilled water and once with 95% ethanol. Samples were counted in a liquid scintillation counter and compared to standard samples prepared in the presence of 0.25, 0.5, and 1.0 pmol/µl of each dNTP.

(10) Cell Cycle Analysis

The cell cycle analysis was performed at flowcytometry core facility of City of Hope National Medical Center. The percent of cells in each phase of the cell cycle was analyzed by ModFit software. The protocol was summarized as below. Cells were trypsinized, washed twice with PBS, and resuspended in 1 ml PBS. 7 ml 0.5 M citric acid buffer (pH 2.35) was added and samples were stored overnight at room temperature in the dark. On the second day, the cells were placed at 4° C. in a dark environment. On the third day, cells were spun down, resuspended in citric acid buffer (pH 4.5) and adjusted to a concentration of 1×10$^6$ cells/ml. On the following day, the cells were spun down and resuspended in 1 ml BSA-H (0.1% BSA in PBS buffer). 150 µg RNase A (DNase free) was added to the solution and cells were incubated at 37° C. for 30 minutes. The cells were washed once with BSA-H and the pellet was resuspended in 1 ml 100 µg/ml propidium iodine (PI) and stored overnight at room temperature in the dark. On the following day, cells were analyzed by flowcytometry (Gao et al. (1998) Biochem Pharmaco 56, 105–112).

Results (1) The Effect of Varying the Time and Sequence of Treatment With HU and Gem on KB Cells The colony-forming ability of KB cells treated with HU and/or Gem was assayed using the ID$_{50}$ concentrations for KB cells. KB cells were exposed to 0.1 mM HU. 0.3 µM Gem was added after 2 to 24 hours of HU treatment, and then cells were assayed for their colony forming ability. When cells were treated with HU or Gem alone, colony formation was reduced to approximately 50% of that seen for untreated controls. When HU and Gem were added together or 2 hours apart, colony-forming ability was similar to that seen for HU or Gem alone. When Gem was added to the growth medium 4 hours after initiation of HU treatment, a markedly enhanced inhibition was observed. It reached a nadir when Gem was added after 8 hours of exposure to HU. Under these conditions, colony formation was reduced by 86% when compared to untreated cells. The inhibition of colony forming ability gradually abated when treatments were separated by 12 to 24 hours but continued to show some enhancement over that seen for either drug alone.

(2) The Effect of HU on the Incorporation of Radiolabeled Gem and CDP Into DNA

The incorporation of $^3$H-labeled Gem into DNA of KB cells treated with HU was measured. When Gem was added to KB cells after 4 hours of HU treatment, three times more $^3$H-labeled Gem was incorporated into DNA than when Gem and HU were added at the same time. Treatment with HU for 8 hours prior to the addition of Gem led to an incorporation rate 6-fold higher than the control. As the separation between treatments increased to 12, 16, and 24 hours, the amount of $^3$H-labeled Gem incorporated into the DNA recovered to levels only slightly higher than that seen with Gem alone. The amount of $^3$H-labeled Gem incorporated into DNA following various combinations of treatment closely parallels the inhibition of colony forming ability, suggesting that the increased incorporation of Gem into DNA was directly related to the increased cytotoxicity as measured by the decreased frequency of colony forming cells. The incorporation of $^3$H-labeled CDP was measured as a control and did not vary significantly for any of the treatment schedules assayed.

(3) Northern and Western Blot of Human Ribonucleotide Reductase M2 Subunit in KB Cells Since expression of hRRM2 is associated with RR activity and is targeted by HU, it was hypothesized that exposure to HU might lead to altered expression of hRRM2 mRNA. Northern blot analysis was used to measure the level of hRRM2 mRNA after exposure to HU at various time points. KB cells growing in logarithmic phase were exposed to 0.1 mM HU and harvested after 0, 2, 4, 8, 12 16 and 24 hours. Total cellular RNA was extracted and analyzed by Northern blot (20 µg per lane). PCR products, consisting of full-length hRRM2 subunit cDNA sequences, were used as probes. The amount of RNA detected was measured by phosphorimager and results were normalized to the amount of GAPDH mRNA detected on the same blot. The amount of hRRM2 mRNA decreased by 20% relative to the untreated sample after 2 hours and then decreased to 60% of control levels at the 4-hour time point. After 8 hours of exposure to HU, hRRM2 mRNA recovery rebounded between 8–12 hours, declined at 16 hours, and then stayed at the same level to 24 hours. To further confirm this phenomenon, Western blot analysis of hRRM2 expression was performed. The hRRM2 protein expression pattern was similar to the Northern blot showing a decrease at the 4-hour point and increased expression afterward.

(4) RR Activity Assay

An in vivo RR activity assay was performed at the same time points as above described. RR activity decreased to 60% of the control after 4 hours of HU exposure, but recovered to the level of the control at the 8-hour point and slightly elevated at 16 hours, and then stayed at the same level at 24 hours. The results are consistent with the observed levels of hRRM2 mRNA and protein expression.

(5) Analysis of Intracellular dNTP Pools

To evaluate the effect of HU on dNTP pools in KB cells, each dNTP pool was measured as described in the Materials and Methods. dATP and dCTP were the most susceptible of the four dNTP pools to inhibition by HU. A decrease in these intracellular pools commenced after 1 hour of exposure to HU. The decline continued, with the dCTP pool reaching a nadir of approximately 15% of the control at 4 hours. The dATP pool reached a nadir after 8 hours. In a second phase, between 8 and 24 hours after exposure to HU, the dATP and dCTP pools slowly recovered to about 80% of their starting level. The dTTP and dGTP pools, however, did not vary significantly over time. The decline and recovery of the dCTP and dATP pools paralleled the results of the colony-forming study. The initial drop in hRRM2 mRNA and protein, observed after 2–4 hours of HU exposure, could contribute to the rapid decline in dCTP and dATP pools seen after 4 hrs, while the subsequent overexpression of hRRM2 mRNA and protein would provide the needed activity to allow gradual recovery of the levels of dCTP and dATP.

(6) Cell Cycle Analysis

To further examine the time- and sequence-dependent interaction between HU and Gem, the effect of HU on cell cycle was studied. The percentage of the cells in S-phase approximately doubled after 4 to 8 hours of exposure to HU, while the percentage of cells in G2/M declined and the percentage of cells in G1 remained stable. After 8 hours of treatment, the fraction of cells in S-phase remained significantly increased relative to untreated cells. As Gem function requires DNA synthesis, the increased percent of cells in S-phase after 4 to 8 hours after exposure to HU is likely to augment its function.

EXAMPLE IV

Phase I Pharmacodynamic Study of Time and Sequence Dependency of Hydroxyurea in Combination with Gemcitabine: a California Cancer Consortium Trial Patents and Methods (1) Patient Selection Between February 1998 and October 1999, 27 patients were entered into this phase I trial. All patients had histologically verified advanced malignancies, unresponsive to previous chemotherapeutic regimens, or for which no "standard" chemotherapeutic regimen existed. Patients were required to have a Karnofsky performance status of of $\geq 60\%$, age $\geq 18$ years, an expected survival of at least 2 months, adequate renal function defined by serum crentinine $\leq 2.0$ mg/dl or 24-h creatinine clearance $\geq 50$ ml/min, adequate bone marrow function defined by an absolute neutrophil count (ANC) >1200/dl and a platelet count $\geq 100,000/\mu l$, and adequate hepatic function defined by a serum bilirubin $\leq 3.0$ mg/dl with aspartate aminotransferase and alanine aminotransferase within five times the upper limit of normal. Prior radiation or chemotherapy must have been completed at least 4 weeks before beginning treatment on this protocol. There was no limit to the number of prior courses of chemotherapy. Pregnant female patients were excluded. All patients gave their voluntary informed consent and signed a consent document that had been reviewed and approved by the City of Hope National Medical Center Institutional Review Board. This trial was also approved by the Cancer Therapy Evaluation Program of the National Cancer Institute (NCI).

(2) Pretreatment Evaluation

All patients had a complete history and physical examination, including documentation of weight, Karnofsky performance status, evaluation for the presence of measurable or evaluable disease, baseline laboratory blood tests, chest radiograph, electrocardiogram, urinalysis, pregnancy test if indicated, and computed tomographic scans of the chest, abdomen, and pelvis as needed to document measurable or evaluable disease. Patients with measurable disease were required to have radiographic procedures for analysis of measurable disease repeated after two cycles of therapy.

(3) Treatment Plan

Hydroxyurea was administered orally at 500 mg every 6 h for four doses on days 1 and 8 of each cycle. Gemcitabine was administered as a 30-min infusion 6 h after the fourth dose of hydroxyurea (i.e., on days 2 and 9). Patients were required to have a platelet count $\geq 75,000/\mu l$ and an ANC $\geq 1,000/dl$ on day 8 to receive chemotherapy. Patients received the chemotherapy as outpatients. Granulocyte colony stimulating factor (G-CSF) was administered beginning on day 10 of all cycles of therapy, including the first cycle. G-CSF was started 24 h after completion of hydroxyurea/gemcitabine administration at a dose of 5 $\mu g/kg$ per day as a single daily subcutaneous injection, and was continued for at least 7 days and until the white blood cell count was greater than $10,000/\mu l$.

(4) Definitions of Dose-limiting Toxicities and the Maximum Tolerated Dose

Hematologic dose-limiting toxicity (DLT) was defined as a platelet count $<75,000/\mu l$ on day 8, or a platelet count $<25,000/\mu l$ lasting seven or more days, an ANC $<1,000/\mu l$ on day 8 or an ANC $<500/\mu l$ lasting seven or more days. Hepatic DLT was defined as bilirubin 4.5–6.0 mg/dl or transaminase 8.0–20.0 times normal (grade 3), and bilirubin >6.0 mg/dl or transaminase more than 20.0 times normal (grade 4). Other toxicities were graded according to the NCI Common Toxicity Criteria Version 1.0. Dose escalations and determination of the maximum tolerated dose (MTD) were based on DLT occurring in the first cycle. MTD was defined as the highest dose tested at which none or only one patient experienced DLT when at least six patients were treated at that dose and were evaluable for toxicity. Patients received additional cycles of therapy until unacceptable toxicity required discontinuation of treatment, the patient requested discontinuation, or disease progression occurred.

(5) Pharmacokinetic Methods

Blood samples for determination of plasma gemcitabine were collected on days 2 and 9 of the first cycle. Samples were collected at the following times: before gemcitabine, just prior to the end of the 30 min infusion, and 5, 10, 15, 30, and 45 min after the end of the infusion. Blood sample were collected in heparinized tubes and kept on ice until plasma could be separated by centrifugation (within 30 min). Plasma was transferred to polypropylene tubes containing tetrahydrouridine to inhibit cytidine deaminase and stored at −70° C. until analysis.

Gemcitabine in plasma was measured by a novel reversed-phase HPLC assay that was developed and validated in the City of Hope Analytical Pharmacology Core Facility. Following addition of the internal standard (IS), 2'3'-dideoxycyditine (Sigma Chemical Company, St. Louis, Mo.), gemcitabine was extracted from plasma by solid-phase extraction using a 1-ml aromatic sulfonic acid cartridge (JT Baker, Phillipsburg, N.J.). Separation of gemcitabine and IS was achieved on a 25×4.6 mm C18 column (Beckman Instruments, Fullerton, Calif.) by gradient elution with a mobile phase consisting of 2–20× methanol in 50 mM $KH_2PO_4$, pH 7.0, at a flow rate of 1 ml/min. Detection was performed by UV absorbance at 275 nm. The standard curve was linear for gemcitabine over the range 200 to 10,000 ng/ml. The inter- and intra-day coefficient of variation across the entire range of the standard curve were <10%, and the accuracies were ±7%. The lower limit of quantification of the assay was 5 ng/ml.

Plasma gemcitabine data were analyzed by compartmental methods using ADAPT II software (USC Biomedical Simulations Resource, Los Angeles, Calif.). Data were fitted to a two-compartment model with first-order elimination. Secondary pharmacokinetic parameters ($CL_{sys}$, V, and $t_{1/2}$) were determined and compared within and among patients.

(6) Statistical Methods

This study was designed as a standard phase I trial to establish the MTD and the DLTs of hydroxyurea and gemcitabine administered in combination. The dose schema is outlined in the treatment section. Secondary pharmacokinetic parameters determined on days 2 and 9 were compared using paired two-tailed t-tests.

Results (1) Patient Characteristics

Enrolled in the study were 27 patients (12 female, 15 male) and 80 cycles of treatment were completed (Table 2). The median age was 55.4 years (range 27–76 years), and the median Karnofsky performance status was 80% (range 60–100%). The predominant tumor types included: adenocarcinoma of the colon or rectum (four), pancreatic cancer (four), non-small-cell lung cancer (three), and head and neck cancers (tonsilar and larynx) (three). Five patients had no prior chemotherapy and the other patients had received one to five prior chemotherapy treatments; 11 patients (41%) had received prior radiation. Patient characteristics are summarized in Table 2.

(2) Patient Evaluability

Of the 27 patients, 24 were evaluable for response and 23 for toxicity and the determination of the MTD. At the dose of 250 mg/m² of gemcitabine on days 2 and 9, a DLT did not permit the continuation of cycle 1 in one patient. As a result, the patient never completed a cycle of therapy and was inevaluable for response. At the dose of 750 mg/m² of gemcitdbine, one patient was replaced because the patient did not receive a complete cycle due to a pleural effusion, and became inevaluable for both toxicity and response. Another patient at this dose was not treated on days 8 and 9 of cycle 1 due to a grade 3 rash, but completed a second cycle. This patient was replaced in the evaluation of toxicity, but was included in the evaluation of response. At the dose of 875 mg/m², one patient was not treated on days 8 and 9 of cycle 1 due to a urinary tract infection, but eventually completed five cycles of therapy. This patient was replaced in the evaluation of toxicity also, but was included in the evaluation of response. Similarly, at the dose of 1,000 mg/m², one patient was not treated on days 8 and 9 of cycle 1 due to urinary tract infection, but completed a second cycle. This patient was also included in the evaluation of response, but not of toxicity. One patient at the same dose completed one cycle, was evaluable for toxicity evaluation, but did not have measurable disease for response evaluation. The rest of the patients were evaluable for both toxicity and response.

TABLE 2

Patient Characteristics

| Number of patients | |
|---|---|
| Total | 27 |
| Male | 12 |
| Female | 15 |
| Age (years) | |
| Median | 55.4 |
| Range | 27–76 |
| Karnofsky performance status | |
| Median | 80 |
| Range | 60–100 |
| Primary site (no. of patients) | |
| Breast | 1 |
| Larynx | 2 |
| Tonsil | 1 |
| Lung | 3 |
| Colon/rectum | 6 |
| Esophagus | 1 |
| Ovary | 1 |
| Pancreas | 4 |
| Stomach | 1 |
| Unknown primary | 2 |
| Gallbladder | 1 |
| Prostate | 2 |
| Testis | 1 |
| Thyroid | 1 |

(3) Toxicities of Therapy

The number of patients treated and the toxicities for the first cycle are summarized in Table 3. Overall, myelosuppression was the DLT. After DLT (grade 4 neutropenia) was observed in two patients at a gemcitabine dose of 1,000 mg/m², a dose level of 875 mg/m² was tested. At 875 mg/m², grade 3 neutropenia developed in one patient on day 8 and grade 4 neutropenia

TABLE 3

Dose Levels, Dose-limiting Toxicities, and Response Data (PLT Thrombocytopenia, ANC Neutropenia)

| | | | | | All cycles | | | | |
|---|---|---|---|---|---|---|---|---|---|
| | First cycle | | | | | | Best response to therapy | | |
| Gemcitabine Dose (mg/m²)[a] | Patients treated | Invaluable for toxicity | DLT Number | Description | Invaluable for response | Cycles completed/ cycles started | Stable disease | Progressive disease | Partial response |
| 250 | 6 | 0 | 1 | PLT | 1 | 22/23 | 3 | 2 | |
| 500 | 3 | 0 | 0 | | 0 | 4/4 | 1 | 2 | |
| 750 | 8 | 2 | 1 | ANC[b] | 1 | 26/28 | 3 | 3 | 1 |
| 875 | 5 | 1 | 2 | ANC[c] | 0 | 17/17 | 4 | 1 | |
| 1000 | 5 | 1 | 2 | ANC[d] | 1 | 11/11 | 1 | 3 | — |
| Total | 27 | 4 | 6 | 5 ANC, 1 PLT | 3 | 80/83 | 12 | 11 | 1 |

[a]30-min infusion on days 2 and 9. The dose of hydroxyurea was fixed at 500 mg every 6 h for four doses on days 1 and 8.
[b]One grade 4 neutropenia (absolute neutrophil count < 500/µl) lasting more than 7 days.
[c]One grade 3 neutropenia on day 8 and one grade 4 neutropenia lasting more than 7 days.
[d]Two grade 4 neutropenias lasting more than 7 days.

developed in another patient. Therefore, the MTD for gemcitabine in this combination of drugs was estimated to be 750 mg/m² on days 2 and 9. A detailed toxicity profile of the eight patients treated at the MTD dose is presented in Table 4.

TABLE 4

Treatment-related Toxicities of Grade 3 or 4 During Cycle 1 at 750 mg/m²

| | Patient number at this dose | | | | | | | | Total |
|---|---|---|---|---|---|---|---|---|---|
| Toxicity | 1 | 2 | 3 | 4 | 5[a] | 6[a] | 7 | 8 | Grade 3/4 |
| Hematology Anemia | 3 | | 3 | | | | 3 | | 3/0 |
| Leukopenia | | | | | 3 | | 3 | 3 | 3/0 |
| Neutropenia | | | | | 3 | | 4 | | 1/1 |
| Thrombocytopenia | 3 | 3 | 3 | 3 | | | | 3 | 5/0 |
| Liver | | | | | | | | 3 | 1/0 |
| Dermatology/rash | | | | | | 3 | | | 1/0 |
| Gastrointestinal | | | | | 3 | | | | 1/0 |
| Neurological | | | | | 3 | | | | 1/0 |
| Total | | | | | | | | | 16/1 |

[a]Patients 5 and 6 missed day 8 of therapy (pleural effusion and rash, respectively) and were replaced for the calculation of DLT/MTD. Patient 6 was eventually able to complete two cycles, and patient 5 was unable to continue.

The one DLT on this arm was the grade 4 neutropenia in patient 7. Patient 5 (primary site gallbladder) with pleural effusion, ascites, and liver nodules made attribution of the gastrointestinal toxicity to the drug unlikely.

(4) Treatment Response

In this study, 24 patients were evaluable for response summarized by dose level in Table 3. One patient who had an unknown primary (retroperitoneal mass and adenopathy) achieved a partial response of 21 months duration. This patient was treated with gemcitabine 750 mg/m². A further 12 patients (50%) had stable disease, three with head and neck cancer, two with lung cancer, two with pancreatic cancer, one with prostate cancer, three with colon cancer and one with breast cancer. Four patients with stable disease were treated with 875 mg/M² of gemcitabine, three patients with 750 mg/m², three patients with 250 mg/m², and one patient each with 1,000 mg/m² and 500 mg/m². Of the 12 patients with stable disease, 4 survived more than 15 months and 3 were alive at the last evaluation, 33 months, 7 months and 5 months from the date of initial treatment. The remaining 11 patients developed progressive disease within 2 months.

(5) Gemcitabine Pharmacokinetics

Day 2 gemcitabine pharmacokinetics were studied in 17 patients and the data from 14 of the 17 patients for both days 2 and 9 were evaluable. Plasma gemcitabine data were best described by a two-compartment model with first-order elimination. Secondary gemcitabine pharmacokinetic parameters determined on day 2 are summarized in Table 5.

TABLE 5

Gemcitabine Pharmacokinetics: Cycle 1, Day 2

| Patient | Dose (mg/m²) | $CL_{sys}$ (l/h/m²) | $V_c$ (l/m²) | $t_{1/2\,alpha}$ (min) | $t_{1/2\,beta}$ (min) |
|---|---|---|---|---|---|
| 1 | 250 | 109.4 | 6.1 | 1.9 | 15.8 |
| 2 | 250 | 106.1 | 6.9 | 2.4 | 13.6 |
| 3 | 250 | 153.9 | 21.9 | 4.8 | 22.6 |
| 4 | 250 | 151.9 | 15.1 | 2.9 | 14.0 |
| 5 | 500 | 45.4 | 3.0 | 2.4 | 10.8 |
| 6 | 750 | 102.4 | 28.1 | 6.9 | 15.7 |
| 7 | 750 | 200.6 | 42.9 | 4.5 | 29.0 |
| 8 | 750 | 36.2 | 1.3 | 1.2 | 14.7 |
| 9 | 750 | 172.1 | 2.6 | 0.3 | 10.0 |
| 10 | 750 | 46.6 | 3.3 | 2.7 | 17.8 |
| 11 | 750 | 31.6 | 0.9 | 0.8 | 12.2 |
| 12 | 875 | 95.8 | 1.1 | 0.3 | 12.2 |
| 13 | 875 | 93.4 | 16.7 | 4.9 | 16.5 |
| 14 | 875 | 126.0 | 11.0 | 2.5 | 18.5 |
| 15 | 1000 | 74.7 | 7.4 | 2.9 | 17.5 |
| 16 | 1000 | 109.3 | 17.4 | 1.6 | 15.0 |
| 17 | 1000 | 86.0 | 4.3 | 1.8 | 11.1 |
| Mean | | 102.4 | 11.2 | 2.7 | 15.7 |
| SD | | 49.8 | 11.5 | 1.8 | 4.9 |

The mean values for $CL_{sys}$, $V_c$, and $t_{1/2}$ estimated in this trial are in good agreement with previously published data for both single-agent gemcitabine and emcitabine used in combination with other anticancer drugs (Venook et al. (2000) J Clin Oncol 18, 2780–2787; Perez-Manga et al. (2000) J Clin Oncol 18, 2545–2552; and Bhargava et al. (2001) Cancer Chemother Pharmacol 48, 95–103). There was no apparent effect of administered dose on gemcitabine $CL_{sys}$ within the range of doses used here. Furthermore, gemcitabine $CL_{sys}$ varied by about 6-fold within a single dose level.

Table 6 summarizes the secondary parameters determined in patients on both day 2 and day 9.

TABLE 6

Gemcitabine Pharmacokinetics: Cycle 1, Day 2 vs. Day 9 (Values are Means ± SD)

| Parameter | Day 2 | Day 9 | P value[a] |
|---|---|---|---|
| $CL_{sys}$ (l/h/m$^2$) | 107.1 ± 52.0 | 97.2 ± 74.3 | 0.7 |
| $V_c$ (l/m$^2$) | 12.0 ± 12.5 | 9.0 ± 9.4 | 0.5 |
| $t_{1/2\ alpha}$ (min) | 2.6 ± 1.9 | 2.4 ± 1.4 | 0.7 |
| $t_{1/2\ beta}$ (min) | 15.2 ± 5.3 | 17.6 ± 7.3 | 0.4 |

[a]Two-tailed paired t-test

There were no significant differences seen in gemcitabine pharmacokinetic parameters determined on day 2 and day 9. However, day-9 pharmacokinetic parameters could not be predicted from the day-2 results, highlighting the significant inter-patient variability.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claim.

What is claimed is:

1. A recombinant isolated nucleic acid comprising:
   a hRPM2 promoter sequence consisting of SEQ ID NO:2, and
   a heterologous nucleotide sequence encoding a transcript, wherein the promoter sequence is operably linked to the heterologous nucleotide sequence.

2. The recombinant isolated nucleic acid of claim 1, wherein the heterologous nucleotide sequence encodes a reporter protein.

3. The recombinant isolated nucleic acid of claim 2, wherein the reporter protein is alkaline phosphatase, horseradish peroxidase, luciferase, β-glactosidase, GFP, or BFP.

4. A recombinant isolated nucleic acid comprising:
   a hRPM2 promoter sequence consisting of SEQ ID NO:3, and
   a heterologous nucleotide sequence encoding a transcript, wherein the promoter sequence is operably linked to the heterologous nucleotide sequence.

5. The recombinant isolated nucleic acid of claim 4, wherein the heterologous nucleotide sequence encodes a reporter protein.

6. The recombinant isolated nucleic acid of claim 5, wherein the reporter protein is alkaline phosphatase, horseradish peroxidase, luciferase, β-glactosidase, GFP, or BFP.

7. A recombinant isolated nucleic acid comprising:
   a hRPM2 promoter sequence consisting of SEQ ID NO:4, and
   a heterologous nucleotide sequence encoding a transcript, wherein the promoter sequence is operably linked to the heterologous nucleotide sequence.

8. The recombinant isolated nucleic acid of claim 7, wherein the heterologous nucleotide sequence encodes a reporter protein.

9. The recombinant isolated nucleic acid of claim 8, wherein the reporter protein is alkaline phosphatase, horseradish peroxidase, luciferase, β-glactosidase, GFP, or BFP.

10. A recombinant isolated nucleic acid comprising:
    a hRPM2 promoter sequence consisting of SEQ ID NO:1, and
    a heterologous nucleotide sequence encoding a transcript, wherein the promoter sequence is operably linked to the heterologous nucleotide sequence.

11. The recombinant isolated nucleic acid of claim 10, wherein the heterologous nucleotide sequence encodes a reporter protein.

12. The recombinant isolated nucleic acid of claim 11, wherein the reporter protein is alkaline phosphatase, horseradish peroxidase, luciferase, β-glactosidase, GFP, or BFP.

* * * * *